US007560227B2

(12) United States Patent
Kim et al.

(10) Patent No.: US 7,560,227 B2
(45) Date of Patent: Jul. 14, 2009

(54) BIOMARKERS OF VULNERABLE ATHEROSCLEROTIC PLAQUES AND METHODS OF USE

(75) Inventors: Young H. Kim, Westborough, MA (US); Ducksoo Kim, Dover, MA (US); Mary Rusckowski, Southborough, MA (US)

(73) Assignee: University of Massachusetts, Boston, MA (US)

( * ) Notice: Subject to any disclaimer, the term of this patent is extended or adjusted under 35 U.S.C. 154(b) by 380 days.

(21) Appl. No.: 11/365,127

(22) Filed: Feb. 28, 2006

(65) Prior Publication Data

US 2007/0207507 A1    Sep. 6, 2007

Related U.S. Application Data

(60) Provisional application No. 60/657,111, filed on Feb. 28, 2005.

(51) Int. Cl.
*C12Q 1/00* (2006.01)
*C07K 7/08* (2006.01)
*C07K 14/00* (2006.01)

(52) U.S. Cl. .......................................... 435/4; 530/326
(58) Field of Classification Search ........................ None
See application file for complete search history.

(56) References Cited

U.S. PATENT DOCUMENTS

| | | | |
|---|---|---|---|
| 5,449,761 | A | 9/1995 | Belinka, Jr. et al. |
| 5,811,394 | A | 9/1998 | Dean |
| 5,976,496 | A | 11/1999 | Dean et al. |
| 6,261,537 | B1 | 7/2001 | Klaveness et al. |
| 6,419,659 | B1 | 7/2002 | Phelps et al. |
| 6,475,159 | B1 | 11/2002 | Casscells et al. |
| 6,475,210 | B1 | 11/2002 | Phelps et al. |
| 6,524,795 | B1 | 2/2003 | Francis et al. |
| 6,580,016 | B2 | 6/2003 | Teirstein et al. |
| 6,615,071 | B1 | 9/2003 | Casscells et al. |
| 2002/0106325 | A1 | 8/2002 | Carpenter |
| 2003/0055307 | A1 | 3/2003 | Elmaleh et al. |
| 2003/0082105 | A1 | 5/2003 | Fischman et al. |
| 2003/0103995 | A1 | 6/2003 | Hamblin et al. |
| 2003/0152566 | A1 | 8/2003 | Schonbeck et al. |

OTHER PUBLICATIONS

Arakawa K., et al., Fluorescence analysis of biochemical constituents identifies atherosclerotic plaque with a thin fibrous cap, Arterioscler Thromb Vasc Biol. Jun. 1, 2002;22(6):1002-7.
Arap, W., et al., Steps toward mapping the human vasculature by phage display, Nat Med. Feb. 2002;8(2):121-7.
Archacki, S.R., et al., Identification of new genes differentially expressed in coronary artery disease by expression profiling, Physiol Genomics. Sep. 29, 2003;15(1):65-74).
Birchler, M., et al., Infrared photodetection for the in vivo localisation of phage-derived antibodies directed against angiogenic markers Journal of Immunological Methods 231 1999.239-248.
Braganza, D.M., & Bennett, M.R., New insights into atherosclerotic plaque rupture, Postgrad Med J 94 2001;77:94-98.
Burke, A., et al., Elevated C-Reactive Protein Values and Atherosclerosis in Sudden Coronary Death, Circulation. 2002;105:2019-2023.
Burke, A. P., et al., Healed Plaque Ruptures and Sudden Coronary Death. Evidence That Subclinical Rupture Has a Role in Plaque Progression, Circulation. 2001;103:934-940.
Chen, J., et al., In vivo imaging of proteolytic activity in atherosclerosis, Circulation 2002, 105: 2766-2771.
Cunningham, B.C., & JA WellsJ.A., High-resolution epitope mapping of hGH-receptor interactions by alanine-scanning mutagenesis, Science Jun. 2, 1989 244: 1081-1085.
Daugherty, A., et al., Myeloperoxidase, a catalyst for lipoprotein oxidation, is expressed in human atherosclerotic lesions. J Clin Invest 1994;94:437-444.
Drevs , J., et al., Effects of PTK787/ZK 222584, a Specific Inhibitor of Vascular Endothelial Growth Factor Receptor Tyrosine Kinases, on Primary Tumor, Metastasis, Vessel Density, and Blood Flow in a Murine Renal Cell Carcinoma Model, Cancer Research 60, 4819-4824, Sep. 1, 2000.
Durier , S., et al., Physiological Genomics of Human Arteries Quantitative Relationship Between Gene Expression and Arterial Stiffness, Circulation. 2003;108:1845-1851.
Flacke, S., et al., Novel MRI Contrast Agent for Molecular Imaging of Fibrin Implications for Detecting Vulnerable Plaques, Circulation. 2001;104:1280-1285.
Forrester, J.S., Prevention of Plaque Rupture: A New Paradigm of Therapy, Ann Intern Med. 2002;137:823-833.
Harisinghani MG, Weissleder R (2004) Sensitive, noninvasive detection of lymph node metastases. PLoS Med 1 (3): e66.
Jaffer, F.A., & Weissleder, R. Seeing Within. Molecular Imaging of the Cardiovascular System, Circ. Res., 2004 94 (4):433-45.
Jaye, D.L., et al.,Use of Real-Time Polymerase Chain Reaction to Identify Cell- and Tissue-Type-Selective Peptides by Phage DisplayAm J Pathol 2003, 162:1419-1429.
Johns, M., et al., In vivo selection of sFv from phage display libraries, J Immunol Methods. May 26, 2000;239 (1-2):137-51.
Kereiakes, D.J., The Emperor's Clothes .In Search of the Vulnerable Plaque, Circulation. 2003;107:2076-2077.

(Continued)

*Primary Examiner*—Suzanne M. Noakes
(74) *Attorney, Agent, or Firm*—Mirick O'Connell DeMallie & Lougee LLP; Roger P. Zimmerman

(57) ABSTRACT

The present invention provides compositions suitable for use as biomarkers of vulnerable plaques as well as methods for the use of such compositions. In preferred embodiments, specific molecular imaging agents are provided that permit the selective identification of vulnerable plaques in coronary and other arteries using non-invasive imaging methods. Such specific molecular imaging agents comprise a binding partner linked to a detectable label that can be used in vivo to visualize vulnerable plaques. In certain preferred embodiments, the binding partner is a peptide that binds selectively to a component of a vulnerable plaque. In other preferred embodiments, the binding partner is an antibody that binds selectively to a component of a vulnerable plaque. In other preferred embodiments, the binding partner is a portion of a polypeptide displayed by a bacteriophage that binds selectively to a component of a vulnerable plaque. In preferred embodiments, the component of a vulnerable plaque is myeloperoxidase or a portion thereof.

3 Claims, 7 Drawing Sheets

OTHER PUBLICATIONS

Kobayashi, S., et al., Interaction of oxidative stress and inflammatory response in coronary plaque instability: important role of C-reactive protein, Arterioscler Thromb Vasc Biol. Aug. 1, 2003;23(8):1398-404. Epub Jun. 12, 2003.

Kolodgie, F.D., et al., Targeting of Apoptotic Macrophages and Experimental Atheroma With Radiolabeled Annexin V A Technique With Potential for Noninvasive Imaging of Vulnerable Plaque, Circulation. 2003;108:3134-3139.

Laakkonen, P., et al., A tumor-homing peptide with a targeting specificity related to lymphatic vessels, Nat Med. Jul. 2002;8(7):751-5. Epub Jun. 10, 2002.

Lafont, A., Basic Aspects Of Plaque Vulnerability, Heart 2003;89:1262-1267.

Litovsky, S., et al., Superparamagnetic iron oxide-based method for quantifying recruitment of monocytes to mouse atherosclerotic lesions in vivo: enhancement by tissue necrosis factor-alpha, interleukin-1beta, and interferon-gamma, Circulation. Mar. 25, 2003;107(11):1545-9.

Mahmood, U and Weissleder, R., Near-Infrared Optical Imaging of Proteases in Cancer, Molecular Cancer Therapeutics, 2, 489-496, May 2003.

Maseri, A., & Fuster, V., Is There a Vulnerable Plaque? Circulation. 2003;107:2068-2071.

Massoud, T.F. & Gambhir, S.S., Molecular imaging in living subjects: seeing fundamental biological processes in a new light, Genes & Development, 3003 17:545-580.

Naghavi, M., et al., From Vulnerable Plaque to Vulnerable Patient. A Call for New Definitions and Risk Assessment Strategies: Part I, Circulation. 2003;108:1664-72.

Naghavi, M., et al., From vulnerable plaque to vulnerable patient: a call for new definitions and risk assessment strategies: Part II. Circulation. Oct. 14, 2003;108(15):1772-8.

Nakamura, M., et al., Identification and treatment of vulnerable plaque. Rev Cardiovasc Med. 2004;5 Suppl 2: S22-33.

New England Biolabs, Instruction manual for Catalog #E8100S, Ph.D.-7™ Phage Display Peptide Library Kit, Version 2.7, Oct. 15, 2003.

Pasterkamp, G., Inflammation of the Atherosclerotic Cap and Shoulder of the Plaque Is a Common and Locally Observed Feature in Unruptured Plaques of Femoral and Coronary Arteries, Arterioscler Thromb Vasc Biol. 1999;19:54-58.

Rioufol, G., et al., Multiple Atherosclerotic Plaque Rupture in Acute Coronary Syndrome. A Three-Vessel Intravascular Ultrasound Study, Circulation. 2002;106:804-808.

Schoenhagen, P., et al., Plaque Vulnerability, Plaque Rupture, and Acute Coronary Syndromes (Multi)-Focal Manifestation of a Systemic Disease Process, Circulation. 2002;106:760-762.

Schwartz, S.M., et al., Molecular Markers, Fibrous Cap Rupture, and the Vulnerable Plaque. New Experimental Opportunities, Circ Res. 2001;89:471-473.

Smith, G.P. & Petrenko, V.A., Phage display, Chem. Rev. 97: 391-410 (1997).

Weissleder, R., et al., In vivo imaging of tumors with protease activated near-infrared fluorescent probes, Nature Biotechnology 17: 375-378 Apr. 1999.

White, S.J., et al., Identification of peptides that target the endothelial cell-specific LOX-1 receptor, Hypertension. Feb. 2001;37(2 Part 2):449-55.

Nicholls, S.J., & Hazen, S.L., Myeloperoxidase and cardiovascular disease, Arterioscler Thromb Vasc Biol. Jun. 2005;25(6):1102-11. Epub Mar. 24, 2005.

Hazell, L.J., & Stocker, R., Oxidation of low-density lipoprotein with hypochlorite causes transformation of the lipoprotein into a high-uptake form for macrophages. Biochem J. 1993;290:165-172.

Smith, G.P., Phage-Display Vectors and Libraries Based on Filamentous Phage Strain fd-tet, 2006, http://www.biosci.missouri.edu/SmithGP/PhageDisplayWebsite/ PhageDisplayWebsiteIndex.html, visited Jun. 29, 2006.

Sugiyama, S., et al., Macrophage myeloperoxidase regulation by granulocyte macrophage colony-stimulating factor in human atherosclerosis and implications in acute coronary syndromes. Am J Pathol 2001;158:879-891.

Thukkani, A.K., et al., Identification of alpha-chloro fatty aldehydes and unsaturated lysophosphatidylcholine molecular species in human atherosclerotic lesions. Circulation 2003;108: 3128-3133.

Bhatia, V, et al., Vulnerable plaques, inflammation and newer imaging modalities.J Postgrad Med. Oct.-Dec. 2003;49(4):361-8.

Burke, AP, et al., Morphological predictors of arterial remodeling in coronary atherosclerosis. Circulation. Jan. 22, 2002;105(3):297-303.

Dobrucki, LW, et al., Molecular imaging. A new approach to nuclear cardiology. Q J Nucl Med Mol Imaging. Mar. 2005;49(1):106-15.

Jaffer, FA, et al., In vivo imaging of thrombin activity in experimental thrombi with thrombin-sensitive near-infrared molecular probe. Arterioscler Thromb Vasc Biol. Nov. 1, 2002;22(11): 1929-35.

MacNeill BD, et al., Intravascular modalities for detection of vulnerable plaque: current status. Arterioscler Thromb Vasc Biol. Aug. 1, 2003;23(8):1333-42. Epub Jun. 12, 2003.

PCT/US06/07111 International Search Report & Written Opinion of the International Searching Authority, mailing date Jul. 9, 2008.

f88-4/Cys6; 9279 bases
CTTGTTCCTATGCTAAGCTTAGCGCTTTGCCGCTNNKNNKNNKTGTNNKNNKNNKNNKNNKCCTGCAGAAGGTGATGACCCGGCTAAAG:TGCTYTTGACTCTCTTCAGGCTTCTGCTACT
GACAAGGATACGATTCGAAACGGCGAAACGGATTGAAACAGGCGAAACAACNKNKNNKCNNKNNKNNKNNKNNKNNKGGACGTCTTCCACTACTGGGCCGATTCGAGAAACTGAGAGAAGTCCGAAGACGATGA L V P M L S F A A X X X C X X X X X X X P A E G D D D P A K A A F D S L Q A S A T
→ Mature pVIII                                                              ← sequencing primer

Figure 5

SEQUENCE LISTING

<160> NUMBER OF SEQ ID NOS: 33

<210> SEQ ID NO 1
<211> LENGTH: 45
<212> TYPE: PRT
<213> ORGANISM: Artificial
<220> FEATURE:
<223> OTHER INFORMATION: pVIII Peptide Display Domain of f88-4/Cys6
      phage
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (15)..(20)
<223> OTHER INFORMATION: Xaa can be any naturally occurring amino acid
<220> FEATURE:
<221> NAME/KEY: misc_feature
<222> LOCATION: (22)..(25)
<223> OTHER INFORMATION: Xaa can be any naturally occurring amino acid

<400> SEQUENCE: 1

Leu Val Pro Met Leu Ser Phe Ala Ala Xaa Xaa Xaa Xaa Cys Xaa Xaa
1               5                   10                  15

Xaa Xaa Xaa Xaa Cys Xaa Xaa Xaa Xaa Pro Ala Glu Gly Asp Asp Pro
            20                  25                  30

Ala Lys Ala Ala Phe Asp Ser Leu Gln Ala Ser Ala Thr
        35                  40                  45

<210> SEQ ID NO 2
<211> LENGTH: 16
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Ala, Arg, Gln, His, or Thr
<220> FEATURE:
<221> NAME/KEY: misc_feature
<222> LOCATION: (2)..(2)
<223> OTHER INFORMATION: Met, Ser, or Val
<220> FEATURE:
<221> NAME/KEY: misc_feature
<222> LOCATION: (3)..(3)
<223> OTHER INFORMATION: Gly, Leu, Lys, Met, or Pro
<220> FEATURE:
<221> NAME/KEY: misc_feature
<222> LOCATION: (4)..(4)
<223> OTHER INFORMATION: Gln, Gly, Leu or Val
<220> FEATURE:
<221> NAME/KEY: misc_feature
<222> LOCATION: (6)..(6)
<223> OTHER INFORMATION: Asn, His, Ser or Trp
<220> FEATURE:
<221> NAME/KEY: misc_feature
<222> LOCATION: (7)..(7)
<223> OTHER INFORMATION: Asp, Leu, Pro,Tyr or Val
<220> FEATURE:
<221> NAME/KEY: misc_feature
<222> LOCATION: (8)..(8)
<223> OTHER INFORMATION: Ala, Asp, Asn or Met
<220> FEATURE:
<221> NAME/KEY: misc_feature
<222> LOCATION: (9)..(9)
<223> OTHER INFORMATION: Arg, Glu or Thr
<220> FEATURE:
<221> NAME/KEY: misc_feature
<222> LOCATION: (10)..(10)
<223> OTHER INFORMATION: Ala, Asn, Gln, Lys or Trp

```
<220> FEATURE:
<221> NAME/KEY: misc_feature
<222> LOCATION: (11)..(11)
<223> OTHER INFORMATION: Ala, Asn, Gly, Ser or Thr
<220> FEATURE:
<221> NAME/KEY: misc_feature
<222> LOCATION: (13)..(13)
<223> OTHER INFORMATION: Ala, Arg, Leu, Thr or Trp
<220> FEATURE:
<221> NAME/KEY: misc_feature
<222> LOCATION: (14)..(14)
<223> OTHER INFORMATION: Ala, Gly, His or Trp
<220> FEATURE:
<221> NAME/KEY: misc_feature
<222> LOCATION: (15)..(15)
<223> OTHER INFORMATION: Ala, Cys, Leu, Lys, Met or Tyr
<220> FEATURE:
<221> NAME/KEY: misc_feature
<222> LOCATION: (16)..(16)
<223> OTHER INFORMATION: Ala, Cys, Gln, Ser or Val

<400> SEQUENCE: 2

Xaa Xaa Xaa Xaa Cys Xaa Xaa Xaa Xaa Xaa Xaa Cys Xaa Xaa Xaa Xaa
1               5                   10                  15

<210> SEQ ID NO 3
<211> LENGTH: 16
<212> TYPE: PRT
<213> ORGANISM: Artificial
<220> FEATURE:
<223> OTHER INFORMATION: Chemically synthesized, clone MPO-1

<400> SEQUENCE: 3

Ala Met Pro Val Cys Ser Leu Asp Arg Lys Ala Cys Thr Ala Tyr Gln
1               5                   10                  15

<210> SEQ ID NO 4
<211> LENGTH: 16
<212> TYPE: PRT
<213> ORGANISM: Artificial
<220> FEATURE:
<223> OTHER INFORMATION: Chemically synthesized, clone MPO-5

<400> SEQUENCE: 4

His Val Leu Gly Cys Ser Tyr Ala Thr Asn Ser Cys Ala His Asn Ala
1               5                   10                  15

<210> SEQ ID NO 5
<211> LENGTH: 16
<212> TYPE: PRT
<213> ORGANISM: Artificial
<220> FEATURE:
<223> OTHER INFORMATION: Chemically synthesized, clone MPO-15

<400> SEQUENCE: 5

Thr Val Met Leu Cys Asn Pro Met Glu Gln Gly Cys Arg Trp Met Cys
1               5                   10                  15

<210> SEQ ID NO 6
<211> LENGTH: 16
<212> TYPE: PRT
<213> ORGANISM: Artificial
<220> FEATURE:
<223> OTHER INFORMATION: Chemically synthesized, clone MPO-17

<400> SEQUENCE: 6

Arg Ser Gly Gln Cys His Asp Asp Thr Trp Asn Cys Leu Ala Cys Val
1               5                   10                  15
```

```
<210> SEQ ID NO 7
<211> LENGTH: 16
<212> TYPE: PRT
<213> ORGANISM: Artificial
<220> FEATURE:
<223> OTHER INFORMATION: Chemically synthesized, clone MPO-4

<400> SEQUENCE: 7

Gln Met Lys Gln Cys Trp Val Asn Thr Ala Thr Cys Trp Gly Leu Ser
1               5                   10                  15

<210> SEQ ID NO 8
<211> LENGTH: 16
<212> TYPE: PRT
<213> ORGANISM: Artificial
<220> FEATURE:
<223> OTHER INFORMATION: Chemically synthesized, clone M3-2

<400> SEQUENCE: 8

Ser Val Glu Gly Cys Thr Tyr Cys Asp Ala Ala Cys Glu Pro Thr Leu
1               5                   10                  15

<210> SEQ ID NO 9
<211> LENGTH: 16
<212> TYPE: PRT
<213> ORGANISM: Artificial
<220> FEATURE:
<223> OTHER INFORMATION: Chemically synthesized, clone M3-3

<400> SEQUENCE: 9

Ala Ser Lys Tyr Cys Gln Met Arg Asn Tyr Trp Cys Gly Cys Ala Gly
1               5                   10                  15

<210> SEQ ID NO 10
<211> LENGTH: 16
<212> TYPE: PRT
<213> ORGANISM: Artificial
<220> FEATURE:
<223> OTHER INFORMATION: Chemically synthesized, clone M3-5

<400> SEQUENCE: 10

Leu Arg Gly Gln Cys Ile Thr Arg Asn Val Ser Cys Glu Pro Lys Pro
1               5                   10                  15

<210> SEQ ID NO 11
<211> LENGTH: 16
<212> TYPE: PRT
<213> ORGANISM: Artificial
<220> FEATURE:
<223> OTHER INFORMATION: Chemically synthesized, clone M3-24

<400> SEQUENCE: 11

Pro Ser Trp Leu Cys Arg Phe Glu Gln Ile Ser Cys Arg Ala Cys His
1               5                   10                  15

<210> SEQ ID NO 12
<211> LENGTH: 16
<212> TYPE: PRT
<213> ORGANISM: Artificial
<220> FEATURE:
<223> OTHER INFORMATION: Chemically synthesized, clone M3-8

<400> SEQUENCE: 12

Gln Gln Ala Val Cys Lys Gln Met Ala Tyr Trp Cys Gly His Gly Asn
1               5                   10                  15

<210> SEQ ID NO 13
```

```
<211> LENGTH: 16
<212> TYPE: PRT
<213> ORGANISM: Artificial
<220> FEATURE:
<223> OTHER INFORMATION: Chemically synthesized, clone M3-11

<400> SEQUENCE: 13

Pro Ala Pro Arg Cys Thr Val Asn Trp Asp Ala Cys Gln Met Gly Leu
1               5                   10                  15

<210> SEQ ID NO 14
<211> LENGTH: 12
<212> TYPE: PRT
<213> ORGANISM: Artificial
<220> FEATURE:
<223> OTHER INFORMATION: Chemically synthesized, clone M3-16

<400> SEQUENCE: 14

Ser Lys Val Leu Cys Phe Asn Tyr Arg Pro Thr Cys
1               5                   10

<210> SEQ ID NO 15
<211> LENGTH: 23
<212> TYPE: PRT
<213> ORGANISM: Artificial
<220> FEATURE:
<223> OTHER INFORMATION: Chemically synthesized, MPO-17 23 mer

<400> SEQUENCE: 15

Arg Ser Gly Gln Cys His Asp Asp Thr Trp Asn Cys Leu Ala Cys Val
1               5                   10                  15

Gly Gly Ser Gly Gly Gly Cys
            20

<210> SEQ ID NO 16
<211> LENGTH: 23
<212> TYPE: PRT
<213> ORGANISM: Artificial
<220> FEATURE:
<223> OTHER INFORMATION: Chemically synthesized, MPO-4 23 mer

<400> SEQUENCE: 16

Gln Met Lys Gln Cys Trp Val Asn Thr Ala Thr Cys Trp Gly Leu Ser
1               5                   10                  15

Gly Gly Ser Gly Gly Gly Cys
            20

<210> SEQ ID NO 17
<211> LENGTH: 23
<212> TYPE: PRT
<213> ORGANISM: Artificial
<220> FEATURE:
<223> OTHER INFORMATION: Chemically synthesized, MPO-1 23 mer

<400> SEQUENCE: 17

Ala Met Pro Val Cys Ser Leu Asp Arg Lys Ala Cys Thr Ala Tyr Gln
1               5                   10                  15

Gly Gly Ser Gly Gly Gly Cys
            20

<210> SEQ ID NO 18
<211> LENGTH: 23
<212> TYPE: PRT
<213> ORGANISM: Artificial
<220> FEATURE:
<223> OTHER INFORMATION: Chemically synthesized, MPO-6 23 mer
```

```
<400> SEQUENCE: 18

His Val Leu Gly Cys Ser Tyr Ala Thr Asn Ser Cys Ala His Asn Ala
1               5                   10                  15

Gly Gly Ser Gly Gly Gly Cys
            20

<210> SEQ ID NO 19
<211> LENGTH: 23
<212> TYPE: PRT
<213> ORGANISM: Artificial
<220> FEATURE:
<223> OTHER INFORMATION: Chemically synthesized, MPO-15 23 mer

<400> SEQUENCE: 19

Thr Val Met Leu Cys Asn Pro Met Glu Gln Gly Cys Arg Trp Met Cys
1               5                   10                  15

Gly Gly Ser Gly Gly Gly Cys
            20

<210> SEQ ID NO 20
<211> LENGTH: 23
<212> TYPE: PRT
<213> ORGANISM: Artificial
<220> FEATURE:
<223> OTHER INFORMATION: Chemically synthesized, M3-2 23 mer

<400> SEQUENCE: 20

Ser Val Glu Gly Cys Thr Tyr Cys Asp Ala Ala Cys Glu Pro Thr Leu
1               5                   10                  15

Gly Gly Ser Gly Gly Gly Cys
            20

<210> SEQ ID NO 21
<211> LENGTH: 23
<212> TYPE: PRT
<213> ORGANISM: Artificial
<220> FEATURE:
<223> OTHER INFORMATION: Chemically synthesized, M3-3 23 mer

<400> SEQUENCE: 21

Ala Ser Lys Tyr Cys Gln Met Arg Asn Tyr Trp Cys Gly Cys Ala Gly
1               5                   10                  15

Gly Gly Ser Gly Gly Gly Cys
            20

<210> SEQ ID NO 22
<211> LENGTH: 23
<212> TYPE: PRT
<213> ORGANISM: Artificial
<220> FEATURE:
<223> OTHER INFORMATION: Chemically synthesized, M3-5 23 mer

<400> SEQUENCE: 22

Leu Arg Gly Gln Cys Ile Thr Arg Asn Val Ser Cys Glu Pro Lys Pro
1               5                   10                  15

Gly Gly Ser Gly Gly Gly Cys
            20

<210> SEQ ID NO 23
<211> LENGTH: 23
<212> TYPE: PRT
<213> ORGANISM: Artificial
<220> FEATURE:
```

```
<223> OTHER INFORMATION: Chemically synthesized

<400> SEQUENCE: 23

Pro Ser Trp Leu Cys Arg Phe Glu Gln Ile Ser Cys Arg Ala Cys His
1               5                   10                  15

Gly Gly Ser Gly Gly Gly Cys
            20

<210> SEQ ID NO 24
<211> LENGTH: 23
<212> TYPE: PRT
<213> ORGANISM: Artificial
<220> FEATURE:
<223> OTHER INFORMATION: Chemically synthesized, M3-8 23 mer

<400> SEQUENCE: 24

Gln Gln Ala Val Cys Lys Gln Met Ala Tyr Trp Cys Gly His Gly Asn
1               5                   10                  15

Gly Gly Ser Gly Gly Gly Cys
            20

<210> SEQ ID NO 25
<211> LENGTH: 23
<212> TYPE: PRT
<213> ORGANISM: Artificial
<220> FEATURE:
<223> OTHER INFORMATION: Chemically synthesized, M3-11 23 mer

<400> SEQUENCE: 25

Pro Ala Pro Arg Cys Thr Val Asn Trp Asp Ala Cys Gln Met Gly Leu
1               5                   10                  15

Gly Gly Ser Gly Gly Gly Cys
            20

<210> SEQ ID NO 26
<211> LENGTH: 16
<212> TYPE: PRT
<213> ORGANISM: Artificial
<220> FEATURE:
<223> OTHER INFORMATION: Chemically synthesized, Clone A3-10

<400> SEQUENCE: 26

Asn Pro Gly Thr Cys Lys Asp Lys Trp Ile Glu Cys Leu Leu Asn Gly
1               5                   10                  15

<210> SEQ ID NO 27
<211> LENGTH: 16
<212> TYPE: PRT
<213> ORGANISM: Artificial
<220> FEATURE:
<223> OTHER INFORMATION: Chemically synthesized, Clone A3-19

<400> SEQUENCE: 27

Asn Leu Ile Trp Cys Arg Lys Glu Phe Ala Arg Cys Thr Ser Asp Met
1               5                   10                  15

<210> SEQ ID NO 28
<211> LENGTH: 16
<212> TYPE: PRT
<213> ORGANISM: Artificial
<220> FEATURE:
<223> OTHER INFORMATION: Clone A3-21

<400> SEQUENCE: 28

Leu Lys Asn Tyr Cys Arg Lys Cys Ser Asn Arg Cys Thr Pro Thr Gly
```

-continued

```
1               5                   10                  15
```

<210> SEQ ID NO 29
<211> LENGTH: 16
<212> TYPE: PRT
<213> ORGANISM: Artificial
<220> FEATURE:
<223> OTHER INFORMATION: Chemically synthesized, Clone A3-12

<400> SEQUENCE: 29

```
Met Asn Tyr Tyr Cys His Gln Thr Thr Lys Thr Cys Arg Thr His Ser
1               5                   10                  15
```

<210> SEQ ID NO 30
<211> LENGTH: 23
<212> TYPE: PRT
<213> ORGANISM: Artificial
<220> FEATURE:
<223> OTHER INFORMATION: Chemically synthesized, A3-10 23 mer

<400> SEQUENCE: 30

```
Asn Pro Gly Thr Cys Lys Asp Lys Trp Ile Glu Cys Leu Leu Asn Gly
1               5                   10                  15

Gly Gly Ser Gly Gly Gly Cys
            20
```

<210> SEQ ID NO 31
<211> LENGTH: 23
<212> TYPE: PRT
<213> ORGANISM: Artificial
<220> FEATURE:
<223> OTHER INFORMATION: Chemically synthesized, A3-19 23 mer

<400> SEQUENCE: 31

```
Asn Leu Ile Trp Cys Arg Lys Glu Phe Ala Arg Cys Thr Ser Asp Met
1               5                   10                  15

Gly Gly Ser Gly Gly Gly Cys
            20
```

<210> SEQ ID NO 32
<211> LENGTH: 23
<212> TYPE: PRT
<213> ORGANISM: Artificial
<220> FEATURE:
<223> OTHER INFORMATION: Chemically synthesized, A3-21 23 mer

<400> SEQUENCE: 32

```
Leu Lys Asn Tyr Cys Arg Lys Cys Ser Asn Arg Cys Thr Pro Thr Gly
1               5                   10                  15

Gly Gly Ser Gly Gly Gly Cys
            20
```

<210> SEQ ID NO 33
<211> LENGTH: 23
<212> TYPE: PRT
<213> ORGANISM: Artificial
<220> FEATURE:
<223> OTHER INFORMATION: Chemically synthesized, A3-12 23 mer

<400> SEQUENCE: 33

```
Met Asn Tyr Tyr Cys His Gln Thr Thr Lys Thr Cys Arg Thr His Ser
1               5                   10                  15

Gly Gly Ser Gly Gly Gly Cys
            20
```

BIOMARKERS OF VULNERABLE ATHEROSCLEROTIC PLAQUES AND METHODS OF USE

RELATED APPLICATIONS

This application claims benefit of U.S. Provisional Patent Application 60/657,111 filed Feb. 28, 2005, the entire contents of which are incorporated by reference for all purposes.

The Sequence Listing submitted herewith as the electronic text file A4059741.txt is hereby incorporated by reference in its entirety.

BACKGROUND OF THE INVENTION

Atherosclerosis is a major health problem with an annual mortality of 500,000 deaths in the United States. It is currently accepted that acute coronary syndromes are most commonly the result of disruption of atheromatous vulnerable plaques that are angiographically modest in severity.

"Vulnerable plaque" is used to refer to a subgroup of only modestly stenotic but unstable plaques that are prone to rupture and, as a result, cause sudden cardiac arrest. While coronary angiography is widely used to illustrate and monitor luminal narrowing of the coronary artery, it is unable to provide selective identification of vulnerable plaques. It is known that approximately one-half of the unstable coronary atherosclerotic plaques are in arteries with 50% or less luminal diameter narrowing. These are lesions that are usually considered insignificant anatomically. Thus, it would be highly desirable if methods and devices were available to detect the unstable atherosclerotic plaque, independent of the degree of luminal diameter narrowing, and treat it before unstable angina and/or acute myocardial infarction and their consequences occur.

In general, atherosclerotic plaque at high risk for rupture contains large lipid pool(s) covered with a thin fibrous cap with ongoing inflammation and neovascularity. Nakamura, M., et al., Identification and treatment of vulnerable plaque. Rev Cardiovasc Med. 2004; 5 Suppl 2:S22-33. Recent reviews of features of vulnerable plaques (Naghavi, M., et al., From Vulnerable Plaque to Vulnerable Patient. A Call for New Definitions and Risk Assessment Strategies: Part I, *Circulation*. 2003; 108:1664-72) have emphasized the interactions of features of the plaque with systemic characteristics (Naghavi, M., et al., From vulnerable plaque to vulnerable patient: a call for new definitions and risk assessment strategies: Part II. Circulation. 2003 Oct. 14; 108(15): 1772-8).

Most of the alternative approaches to identify vulnerable plaques are based on often risky invasive endovascular approaches. Therefore, the development of non-invasive technology which enables vulnerable plaques to be distinguished from stable ones, is critical and urgently needed to reduce the morbidity and mortality of atherosclerotic patients.

Molecular approaches have been used to the problem of detecting and treating vulnerable plaques. Phage display has been used to identify peptide motifs that home to specific vascular beds (Arap, W., et al., Steps toward mapping the human vasculature by phage display, Nat. Med. 2002 February; 8(2):121-7), tumor lymphatics (Laakkonen, P., et al., A tumor-homing peptide with a targeting specificity related to lymphatic vessels, Nat Med. 2002 July; 8(7):751-5. Epub 2002 Jun 10) and a endothelial cell-specific LOX-1 receptor (White, S. J., et al., Identification of peptides that target the endothelial cell-specific LOX-1 receptor, Hypertension. 2001 February; 37(2 Part 2):449-55). See also Johns, M., et al., In vivo selection of sFv from phage display libraries, J Immunol Methods. 2000 May 26; 239(1-2):137-51 and Litovsky, S., et al., Superparamagnetic iron oxide-based method for quantifying recruitment of monocytes to mouse atherosclerotic lesions in vivo: enhancement by tissue necrosis factor-alpha, interleukin-1 beta, and interferon-gamma, Circulation. 2003 Mar. 25; 107(11):1545-9. In other studies, genes differentially expressed in plaques have been studied using suppression substractive hybridization (Faber, B. C., et al., Identification of genes potentially involved in rupture of human atherosclerotic plaques, Circ Res. 2001 Sep. 14; 89(6):547-54) and hybridization to oligonucleotide microarrays (Archacki, S. R., et al., Identification of new genes differentially expressed in coronary artery disease by expression profiling, Physiol Genomics. 2003 Sep. 29; 15(1):65-74).

An effective imaging approach for detection of vulnerable plaque should be based on the underlying biology. Knowing what lies within a plaque is a way to anticipate and prevent future events. A marker that can indicate the composition of the lesion is needed to predict the risk of plaque rupture. Myeloperoxidase, an enzyme released by activated macrophages may be one of those markers.

Myeloperoxidase is a heme containing enzyme, composed two 55 kDa subunits and two 15 kDa subunit, that uses $H_2O_2$ as a substrate to generate products that oxidize lipids and proteins. One such product, hypochlorous acid (HOCl), is critical in host defense against bacteria, viruses and tumor cells, and can also cause injury to normal tissue such as vascular epithelium. There is evidence that myeloperoxidase is generated and released by macrophages in plaque, and is believed to contribute to atherogenesis by catalyzing oxidative reactions (Daugherty, A., et al., Myeloperoxidase, a catalyst for lipoprotein oxidation, is expressed in human atherosclerotic lesions. J Clin Invest 1994; 94:437-444). Plaque rupture is consistent with a thin fibrous cap as well as high macrophage content, and these macrophages are known to secrete myeloperoxidase extracellularly in response to activation (Klebanoff, S. F., Oxygen metabolism and the toxic properties of phagocytes. Ann Int Med. 1980; 93:480-489). Immunohistochemistry has demonstrated an increased number of myeloperoxidase-expressing macrophages in eroded or ruptured plaques (Sugiyama, S., et al., Macrophage myeloperoxidase regulation by granulocyte macrophage colony-stimulating factor in human atherosclerosis and implications in acute coronary syndromes. Am J Pathol 2001; 158:879-891), with myeloperoxidase and macrophages found to co-localize in sections of atherogenic lesions. There has also been shown to be widespread immunostaining of myeloperoxidase consistent with both intra- and extracellular distributions of the enzyme in macrophage rich areas, and intense foci of immunostaining for myeloperoxidase in lipid rich regions of advanced atherosclerotic lesions. Myeloperoxidase oxidation of lipoproteins is believed to increase the negative charge thus forming products that stimulate cholesterol deposition in macrophages (Hazfil, L. J., & Stocker, R., Oxidation of low-density lipoprotein with hypochlorite causes transformation of the lipoprotein into a high-uptake form for macrophages. Biochem J. 1993; 290:165-172).

Myeloperoxidase generated HOCl was also found to promote selective oxidative cleavage of plasmalogens, liberating chloro fatty aldehydes and unsaturated lysophosphatidylcholine in human atherosclerotic lesions (Thukkani, A. K., et al., Identification of alpha-chloro fatty aldehydes and unsaturated lysophosphatidylcholine molecular species in human atherosclerotic lesions. Circulation 2003; 108: 3128-3133). Myeloperoxidase is believed to play a critical role in the development of atherosclerotic lesions by augmenting oxidative stress. Myeloperoxidase, as a component of atherosclerotic lesions, is a marker that can indicate the composition of the lesion as a marker of vulnerable plaques.

SUMMARY OF THE INVENTION

The present invention provides compositions suitable for use as biomarkers of vulnerable plaques as well as methods for the use of such compositions. In preferred embodiments, specific molecular imaging agents are provided that permit the selective identification of vulnerable plaques in coronary and other arteries using non-invasive imaging methods. Such specific molecular imaging agents comprise a binding partner linked to a detectable label that can be used in vivo to visualize vulnerable plaques. In certain preferred embodiments, the binding partner is a peptide that binds selectively to a component of a vulnerable plaque. In other preferred embodiments, the binding partner is an antibody that binds selectively to a component of a vulnerable plaque. In other preferred embodiments, the binding partner is a portion of a polypeptide displayed by a bacteriophage that binds selectively to a component of a vulnerable plaque. In preferred embodiments, the component of a vulnerable plaque is myeloperoxidase or a portion thereof.

In preferred embodiments, the present invention provides an isolated polypeptide having 16-200 amino acid residues, comprising the sequence (SEQ ID NO:2)

$$-Xaa_1-Xaa_2-Xaa_3-Xaa_4-Cys_5-Xaa_6-Xaa_7-Xaa_8-Xaa_9-Xaa_{10}-Xaa_{11}-Cys_{12}-Xaa_{13}-Xaa_{14}-Xaa_{15}-Xaa_{16}-$$

wherein $Xaa^1$ is an amino acid residue selected from the group consisting of Ala, Arg, Gln, His and Thr; $Xaa_2$ is an amino acid residue selected from the group consisting of Met, Ser and Val; $Xaa_3$ is an amino acid residue selected from the group consisting of Gly, Leu, Lys, Met and Pro; $Xaa_4$ is an amino acid residue selected from the group consisting of Gln, Gly, Leu and Val; $Xaa_6$ is an amino acid residue selected from the group consisting of Asn, His, Ser and Trp; $Xaa_7$ is an amino acid residue selected from the group consisting of Asp, Leu, Pro, Tyr and Val; $Xaa_8$ is an amino acid residue selected from the group consisting of Ala, Asp, Asn and Met; $Xaa_9$ is an amino acid residue selected from the group consisting of Arg, Glu and Thr; $Xaa_{10}$ is an amino acid residue selected from the group consisting of Ala, Asn, Gln, Lys and Trp; $Xaa_{11}$ is an amino acid residue selected from the group consisting of Ala, Asn, Gly, Ser and Thr; $Xaa_{13}$ is an amino acid residue selected from the group consisting of Ala, Arg, Leu, Thr and Trp; $Xaa_{14}$ is an amino acid residue selected from the group consisting of Ala, Gly, His, and Trp; $Xaa_{15}$ is an amino acid residue selected from the group consisting of Asn, Cys, Leu, Met, and Tyr; and $Xaa_{16}$ is an amino acid residue selected from the group consisting of Ala, Cys, Gln, Ser and Val. Preferably the isolated polypeptide binds specifically to a component of a vulnerable plaque. In certain preferred embodiments, the isolated polypeptide binds specifically to myeloperoxidase.

More generally, the present invention provides an isolated polypeptide that binds specifically to a component of a vulnerable plaque and having 16-200 amino acid residues, comprising the sequence (SEQ ID NO:2)

$$-Xaa_1-Xaa_2-Xaa_3-Xaa_4-Cys_5-Xaa_6-Xaa_7-Xaa_8-Xaa_9-Xaa_{10}-Xaa_{11}-Cys_{12}-Xaa_{13}-Xaa_{14}-Xaa_{15}-Xaa_{16}-$$

wherein $Xaa_1$ is an amino acid residue selected from the group consisting of Ala, Arg, Gln, His, Leu, Pro, Ser and Thr; $Xaa_2$ is an amino acid residue selected from the group consisting of Ala, Arg, Gln, His, Lys, Met, Ser and Val; $Xaa_3$ is an amino acid residue selected from the group consisting of Ala, Glu, Gly, Leu, Lys, Met, Pro, Trp and Val; $Xaa_4$ is an amino acid residue selected from the group consisting of Arg, Gln, Gly, Leu, Tyr and Val; $Xaa_6$ is an amino acid residue selected from the group consisting of Arg, Asn, Gln, His, Ile, Lys, Phe, Ser, Thr and Trp; $Xaa_7$ is an amino acid residue selected from the group consisting of Asp, Asn, Gln, Leu, Met, Phe, Pro, Thr, Tyr and Val; $Xaa_8$ is an amino acid residue selected from the group consisting of Ala, Arg, Asp, Asn, Cys, Glu, Met and Tyr; $Xaa_9$ is an amino acid residue selected from the group consisting of Ala, Arg, Asn, Gln, Glu, Thr and Trp; $Xaa_{10}$ is an amino acid residue selected from the group consisting of Ala, Asp, Gln, Ile, Lys, Pro, Thr, Tyr, Trp and Val; $Xaa_{11}$ is an amino acid residue selected from the group consisting of Ala, Asn, Gly, Ile, Lys, Pro, Ser, Thr and Trp; $Xaa_{13}$ is an amino acid residue selected from the group consisting of Arg, Cys, Gly, Gln, Glu, Leu, Thr and Trp; $Xaa_{14}$ is an amino acid residue selected from the group consisting of Ala, Cys, Gly, His, Leu, Met, Pro and Trp; $Xaa_{15}$ is an amino acid residue selected from the group consisting of Ala, Cys, Gly, His, Leu, Lys, Met, Thr and Tyr; and $Xaa_{16}$ is an amino acid residue selected from the group consisting of Asn, Cys, Gln, Gly, His, Leu, Pro, Ser and Val. In other embodiments, the invention provides isolated polypeptides having conservative amino acid substitutions as described below.

In other embodiments, the present invention provides an isolated polypeptide having 16-100 amino acid residues, consisting essentially of an isolated polypeptide having sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13. In preferred embodiments, the present invention provides an isolated polypeptide having 16-23 amino acid residues, consisting essentially of an isolated polypeptide having sequence selected from the group consisting of SEQ ID NO:3, SEQ ID NO:4, SEQ ID NO:5, SEQ ID NO:6, SEQ ID NO:7, SEQ ID NO:15, SEQ ID NO:16, SEQ ID NO:17 and SEQ ID NO:18. In preferred embodiments the isolated polypeptide binds specifically to a component of a vulnerable plaque. In particularly preferred embodiments the isolated polypeptide binds specifically to myeloperoxidase.

In other preferred embodiments, the present invention provides an isolated polypeptide having 16-100 amino acid residues, consisting essentially of an isolated polypeptide having sequence selected from the group consisting of SEQ ID NO:26, SEQ ID NO:27, SEQ ID NO:28, SEQ ID NO:29, SEQ ID NO:30, SEQ ID NO:31, SEQ ID NO:32 and SEQ ID NO: 33. In preferred embodiments the isolated polypeptide binds specifically to a component of a solid tumor. In particularly preferred embodiments, the isolated polypeptide binds specifically to TAG-72.

The polypeptides are preferably linked to a detectable label. Suitable detectable labels include radionuclides, such as $^{99m}$Tc, fluorophores, including both chemical fluorophores and physical fluorophores such as quantum dots, as well as labels detected by a specific interaction, such as biotin. In certain preferred embodiments, the polypeptides are labeled with $^{99m}$Tc for nuclear medicine imaging applications. In other preferred embodiments, the polypeptides are labeled with nano- or submicron magnetic or paramagnetic particles for magnetic resonance imaging applications. In further embodiments, the polypeptides are labeled with nano- or submicron echogenic particles for diagnostic or therapeutic ultrasound applications, both endovascular and non-endovascular. In yet further embodiments, the polypeptides are labeled with nano- or submicron fluorescent particles or photolabile tags for fluorescence imaging, photodynamic imaging, visualization or phototherapy. In other embodiments, the polypeptides are labeled with nano- or submicron chips for transmitting or receiving information. In other embodiments, the polypeptides are labeled with nano- or submicron devices. In yet other embodiments, the polypeptides are associated with therapeutic drugs, chemicals, genes, antibodies, or microorganisms for removal or dissolution or protection of the plaques.

In certain preferred embodiments, the polypeptide is constrained by a disulfide bond linking $Cys_5$ to $Cys_{12}$, producing a cyclic peptide. In other preferred embodiments, the polypeptide is linear in the region $Xaa_1$ to $Xaa_{16}$. Typically, the isolated polypeptide is part of a composition including pharmaceutically acceptable carrier suitable for parenteral or oral administration. In general, when used as a diagnostic reagent, an amount sufficient for at least one dose of the composition comprising the labeled isolated polypeptide and a pharmaceutically acceptable carrier is provided in a kit with instructions for use.

The isolated polypeptides may be used as a single molecular species or as compositions comprising at least two molecular species. This approach is especially useful if different isolated polypeptides specifically bind to different components of a vulnerable plaque, or different sites on the same component. In this aspect, the present invention provides in certain embodiments a collection of isolated polypeptides having the sequences SEQ ID NO:3, SEQ ID NO:4, SEQ ID NO:5, SEQ ID NO:6, SEQ ID NO:7, SEQ ID NO:15, SEQ ID NO:16, SEQ ID NO:17 and SEQ ID NO:18. In other embodiments, the present invention provides a collection of isolated polypeptides having the sequences SEQ ID NO:26, SEQ ID NO:27, SEQ ID NO:28, SEQ ID NO:29, SEQ ID NO:30, SEQ ID NO:31, SEQ ID NO:32 and SEQ ID NO: 33. In further embodiments, the invention provides compositions that include at least two isolated polypeptides from such a collection of isolated polypeptides, each conjugated to a detectable label selected from the group consisting of radionuclides, fluorophores and biotin, and a pharmaceutically acceptable carrier. In other embodiments, the invention provides multivalent reagents comprising one or more molecular species of the isolated polypeptides linked to using frameworks such as MAP (multiple antigenic peptides) and polyvalent branched PEG (polyethylene glycol).

In certain preferred embodiments, the isolated polypeptide can be produced by recombinant means in a suitable cell using a vector comprising a nucleotide sequence encoding the isolated polypeptide operatively linked to a promoter. The cell may be an eukaryotic cell or a prokaryotic cell. Such embodiments typically include a cell comprising such a vector. In other embodiments, the invention provides for the use of the isolated polypeptide for the manufacture of a reagent for the detection of a vulnerable plaque. In other aspects, the present invention A method of detecting a vulnerable plaque comprising the steps of providing an isolated polypeptide that binds specifically to a component of a vulnerable plaque that is conjugated to a detectable label; contacting a vulnerable plaque with the labeled isolated polypeptide; and detecting the detectable label thereby detecting the vulnerable plaque. In preferred embodiments the method further includes the step of imaging the spatial position of the detected vulnerable plaque.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 is a diagram of the sequence of the display domain of mature pVIII of the f88-4/Cys6 library, showing the amino acid sequence of the display domain of the mature pVIII, SEQ ID NO:1, the nucleotide sequence of the display domain, SEQ ID NO:34, and the nucleotide seciuence of the sequencing primer. SEQ ID NO:35.

As shown in FIG. 7A, upon incubation of the MPO-17 peptide with the myeloperoxidase, a gradual shift was observed for to a retention time associated with myeloperoxidase. For example, the UV peak for the enzyme increased from 16% of total protein at 5 mm of incubation to 46% of total protein after 2 h incubation. FIG. 7B shows no shift over a comparable time period for incubation of myeloperoxidase with the control twenty-three mer peptide.

Figure 9A, anti-myeloperoxidase antibody followed with biotinylated secondary antibody; FIG. 9B, biotinylated twenty-three mer MPO-17 peptide; FIG. 9C, biotinylated twenty-three mer control peptide; FIG. 9D, incubated with both the biotinylated twenty-three mer MPO-17 peptide and the biotinylated twenty-three mer control peptide, without primary antibody. Each slide was treated with an anti-biotin antibody and the ABC alkaline phosphatase kit (Vector labs) and counterstained with hematoxylin. The anti-myeloperoxidase antibody shows the presence of myeloperoxidase red staining (FIG. 9A). Only the bkie hematoxylin stain is observed when the tissue is treated with the control peptide (FIG. 9C) or in the absence of the primary antibody (FIG. 9D). However, treatment with the twenty-three mer MPO-17 peptide produces a staining pattern similar to that seen with the anti-myeloperoxidase antibody (FIG. 9B).

DETAILED DESCRIPTION OF THE INVENTION

Figure 1A:
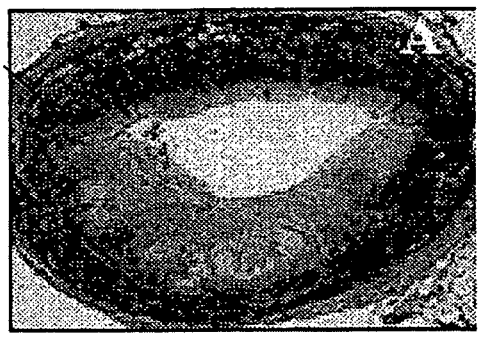
FIG. 1A shows a cross sectional view of a nonvulnerable plaque showing fibrous tissue that partially blocks blood flow but not likely to cause a clot or cardiac event.
Figure 1B:
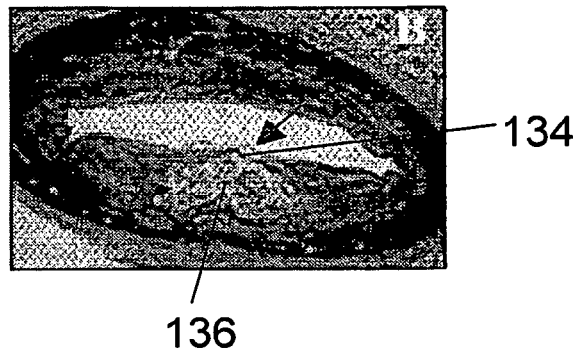
FIG. 1B shows a cross sectional view of a vulnerable plaque with a lipid rich core 136 and a thin fibrous cap 134.

Vulnerable plaques are characterized by a thin fibrous cap with a lipid-rich core, and marked cellular infiltration containing monocytes, macrophages, and foam cells (FIG. 1A, FIG. 1B). Improved imaging and diagnostic modalities are required that are capable of visualizing these features and moreover to predict which of the atherosclerotic plaques are prone to rupture, thereby distinguishing stable from vulnerable plaque. Several invasive and noninvasive imaging techniques are available to assess atherosclerotic vessels. Most of the techniques identify the luminal diameter, the volume, and the thickness of the plaque. However, none of the current imaging techniques are capable of characterizing biological plaque activity to identify high-risk patients with vulnerable plaque. Vulnerable plaques have been assessed with catheter-based intravascular ultrasound, optical coherence tomography, angioscopy, and thermography. All of these modalities, albeit capable of high-resolution imaging, rely primarily on the detection of structural abnormalities and require invasive endovascular access.

Figure 2A:
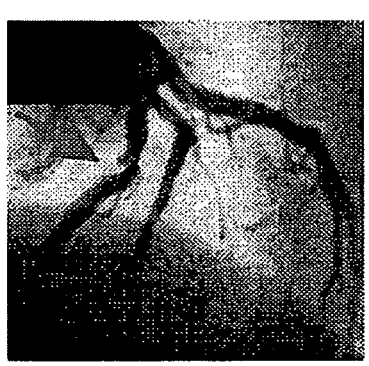
FIGS. 2A, 2B and 2C show plaques as visualized by angiography (FIG. 2A), multidetector computed tomography (FIG. 2B and FIG. 2C), showing a plaque (arrow 80, FIGS. 2B and 2C) at the proximal portion of the left anterior descending artery.
Figure 2B:
Figure 2C:

Multidetector Computed Tomography (MDCT) is a new non-invasive imaging technique for detecting coronary artery disease. MDCT allows direct visualization of the lumen of coronary arteries, as well as plaque within the artery (FIG. 2). Despite its high quality, non-invasive imaging, distinction of vulnerable plaque from non-vulnerable ones is difficult using MDCT. Single Photon Emission Computed Tomography (SPECT) and Positron Emission Tomography (PET) provide useful functional information on diseased organs or tissues; however, their restricted spatial resolution limits clinical application on detection of vulnerable plaque without a suitable agent of high affinity.

It is understood that the detectable label is appropriately chosen for the method of detection, e.g., superparamagnetic iron oxide or gadolinium would be suitable for detection using MRI, an enzyme sensitive near-infrared fluorescence probe would be suitable for fluorescence-mediated tomography (Chen, J., et al., In vivo imaging of proteolytic activity in atherosclerosis, Circulation 2002, 105: 2766-2771). See, generally, Massoud, T. F. & Gambhir, S. S., Molecular imaging in living subjects: seeing fundamental biological processes in a new light, Genes & Development, 3003 17:545-580 and Jaffer, F. A., & Weissleder, R. Seeing Within. Molecular Imaging of the Cardiovascular System, Circ. Res., 2004 94(4):433-45.

Figure 3:
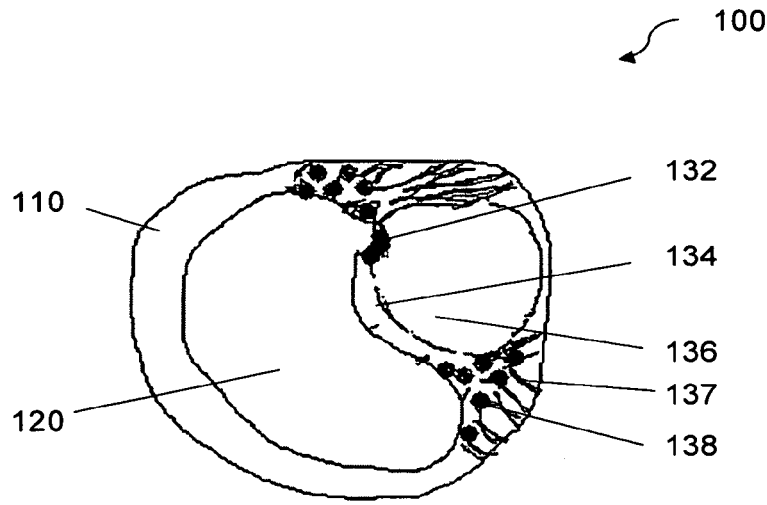
FIG. 3 is a diagrammatic representation of a transverse section through a vulnerable plaque.

Characteristic histopathologic features of vulnerable plaques have been described (e.g., U.S. Pat. No. 6,615,071). Such features include: a lipid core containing a substantial amount of free and esterified cholesterol, and other necrotic debris; infiltrated macrophages (and less frequently lymphocytes, monocytes and mast cells); less abundant smooth muscle cells; and, consequentially, low content of collagen and other matrix proteins. FIG. 3 is a schematic diagram of a transverse section 100 through an artery showing the arterial wall 110 and lumen and showing major features of the vulnerable plaque, including a fibrous cap 134 having a rupture point 132, a lipid core 136, angiogenic structures 137 and cellular infiltrate, including macrophages 138. The lipid core characterizing most ruptured plaque is mainly a large pool of cholesterol resulting from insudation and from the release of the contents of foam cells following degradation of the cell wall. The low content of collagen and matrix proteins associated with at-risk plaque contributes to an important feature of the unstable plaque—the thin plaque cap. The release of matrix-digesting enzymes by the inflammatory cells is thought to contribute to plaque rupture. Small blood clots, particularly microthrombi, are also frequently found on non-ruptured but inflamed ulcerated plaque surfaces. The rupture process is not completely understood, but it is known that the plaques most likely to rupture are those that have both a thin collagen cap 134 (fibrous scar) and a point of physical weakness in the underlying plaque, a rupture point 132. Such points are thought to be located (as determined by modeling studies and pathologic analysis) at junctures where pools of cholesterol meet a more cellular and fibrous part of the plaque. It has been observed that plaques with inflamed surfaces or a high density of activated macrophages and a thin overlying cap are at risk of thrombosis.

Figure 4:
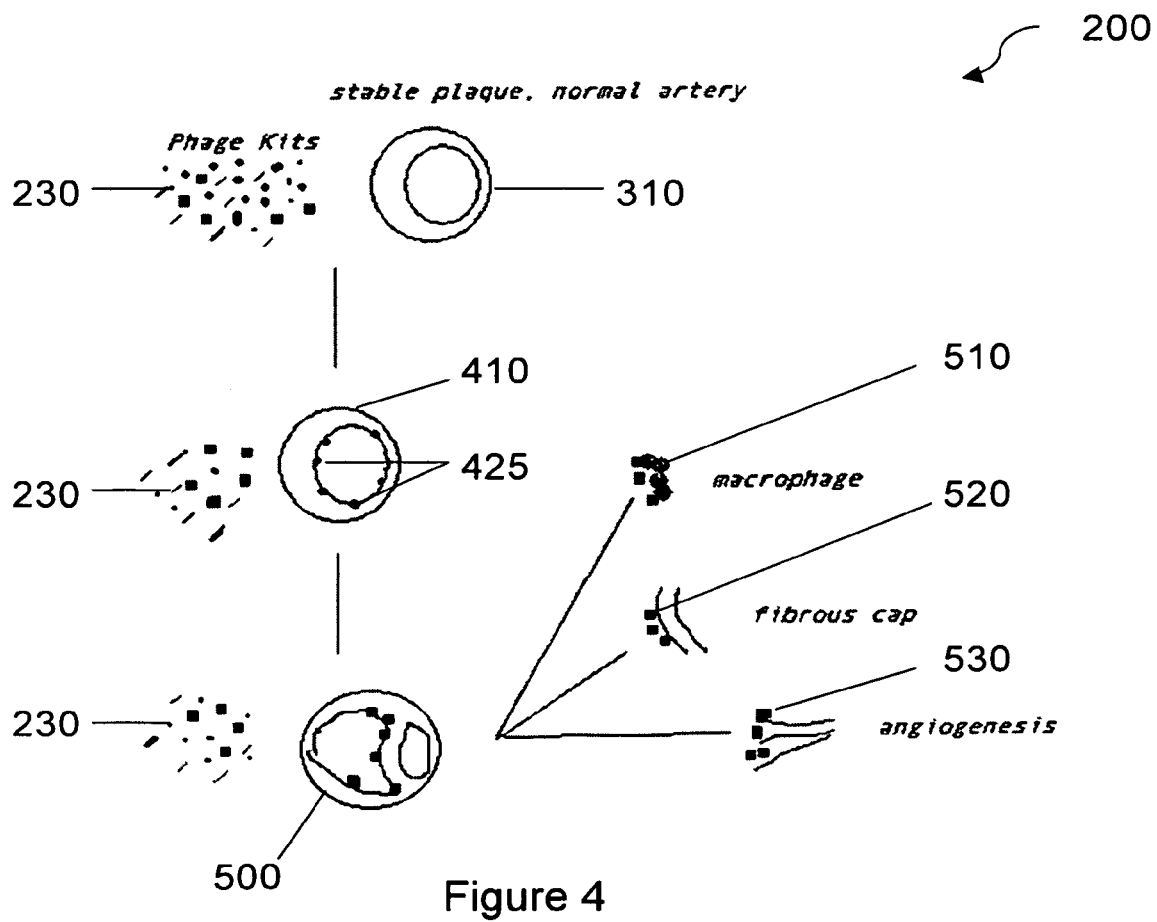
FIG. 4 is a schematic diagram of the process of using phage display kits for identifying peptides and antibodies specific for components (macrophages, fibrous cap and angiogenesis) of a vulnerable plaque.
Figure 6:
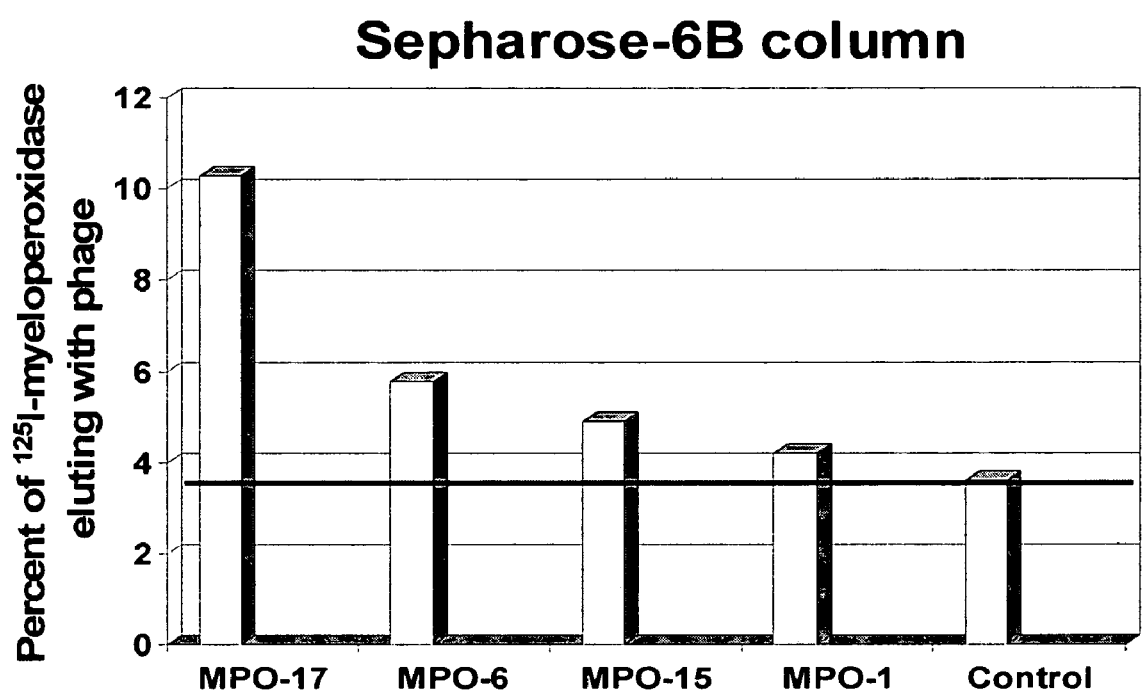
FIG. 6 is a graphical representation of the results of studies of the binding of several phage clones to $^{125}$-myeloperoxidase where the relative magnitude of binding was MPO-17>MPO- 6>MPO-15 >MPO-1 >control (MPO-4). The consensus phage clones were radiolabeled with $^{99m}$Tc, using mercaptoacetyltriglycine (MAG$_3$) as chelator, and the myeloperoxidase was iodinated using iodogen. The $^{99m}$Tc-phage were incubated with the $^{125}$I-myeloperoxidase for 15-30 minutes, and then separated on a Sepharose 6B column. The shift of $^{125}$I to the higher molecular weight fractions associated with $^{99m}$Tc-phage indicated binding.

FIG. 4 is a schematic diagram of the process of using phage display kits or phage libraries 230 for identifying peptides and antibodies specific for components associated with macrophages 510, components associated with the fibrous cap and components associated with angiogenesis 530 in a vulnerable plaque. In preferred embodiments, the markers show differential binding to stable plaques in normal artery 310 relative to developing vulnerable plaques 410, 425 and advanced vulnerable plaques 500.

In some embodiments, the present invention includes polypeptides modified by conservative substitutions of selected amino acid residues. In this regard, it is understood that amino acids may be substituted on the basis of side chain bulk, charge and/or hydrophobicity. Amino acid residues are classified into four major groups:

Acidic: The residue has a negative charge due to loss of H ion at physiological pH and the residue is attracted by aqueous solution so as to seek the surface positions in the conformation of a peptide in which it is contained when the peptide is in aqueous solution.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

Amino acid residues can be further classified as cyclic or non-cyclic, aromatic or non aromatic with respect to their side chain groups these designations being commonplace to the skilled artisan.

Commonly encountered amino acids which are not encoded by the genetic code, include 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparagine (EtAsn) for Asn, and Gln; Hydroxyllysine (Hyl) for Lys; allohydroxyllysine (AHyl) for Lys; 3-(and 4)hydroxyproline (3Hyp, 4Hyp) for Pro, Ser, and Thr; allo-isoleucine (AIle) for Ile, Leu, and Val; ρ-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I)phenylalanine, triflourylphenylalanine, for Phe.

TABLE 1

| Original Residue | Exemplary Conservative Substitution | Preferred Conservative Substitution |
|---|---|---|
| Ala | Val, Leu, Ile | Val |
| Arg | Lys, Gln, Asn | Lys |

TABLE 1-continued

| Original Residue | Exemplary Conservative Substitution | Preferred Conservative Substitution |
|---|---|---|
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala Phe | Leu |
| Leu | Ile, Val Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe Ala | Leu |

In other embodiments, the following unusual or unnatural amino acid substitutions, singly or in combination, may be used: β-alanine, homoproline, hydroxyproline, L-3-(2'-naphthyl)-alanine, D-3-(2'-naphthyl)-alanine, 1-aminocyclopentanecarboxlic acid, sarcosine, β thienyl-L-alanine, β-thienyl-D-alanine, D-3-(3-pyridyl)-alanine, aminoctanoic acid, aminocaproic acid, 7-aminoheptanoic acid, aminovaleric acid, S-acetamidomethyl-D-cysteine, S-acetamidomethyl-L-cysteine, t-butyl-D-cysteine, t-butyl-L-cysteine, S-ethyl-D-cysteine, S-ethyl-L-cysteine, L-aspartic acid(beta-benzyl ester), D-aspartic acid(β-benzyl ester), L-glutamic acid (gamma-benzyl ester), D-glutamic acid(gamma-benzyl ester), N-epsilon-2(2-chloro-CBZ)-L-lysine, N-epsilon-(2-chloro-CBZ)-D-lysine, N-epsilon-(CBZ)-L-lysine, N-epsilon-(CBZ)-D-lysine, p-chloro-D-phenylalanine, p-nitro-L-phenylalanine, L-serine (OBzl), D-serine(OBzl), D-threonine(OBzl), L-threonine(OBzl), O-(2,6-dichlorobenzyl)-L-tyrosine, O-t-butyl-L-tyrosine, and O-t-butyl-D-tyrosine.

A useful method for identification of certain residues or regions of a polypeptide for amino acid substitution other than those described herein for receptor specificity is called alanine scanning mutagenesis as described by Cunningham and Wells (1989) Science, 244: 1081-1085. Here a residue or group of target residues are identified (e.g. charged residues such as Arg, Asp, His, Lys, and Glu) and replaced by a neutral or negatively charged amino acid to affect the interaction of the amino acids with the surrounding aqueous environment in or outside the cell. Those domains demonstrating functional sensitivity to the substitution then are refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed polypeptide screened for the optimal combination of desired activity.

Phage-display screening is a powerful molecular tool to search for specific peptide sequences of high affinity to unknown molecular markers present only in vulnerable plaques. The M13 phage bacteriophage infects bacteria and non-infectious to humans. The non-lytic phage M13 is a 900 nm long, 6.5 nm diameter filament with a single stranded circular DNA genome encoding 10 proteins. Capsid proteins g3p and g8p can present foreign protein sequences fused to their N-termini. Such domains include antibody fragments (scFv and Fab'), peptides, enzymes and enzyme inhibitors. Different combinations of amino acids can be inserted into the capsid protein or replace part of the protein by recombinant DNA technology, generating a library of phages harboring tens of billions of different capsid proteins.

The recent development of combined SPECT/CT or PET/CT has resulted in functional and anatomical information that can be depicted on the fused images. Biomarkers such as specific binding agents linked to detectable labels that can differentiate a vulnerable plaque from a stable one are useful for diagnostic purposes, especially in clinical applications such as SPECT/CT or PET/CT.

Such biomarkers are identified by screening combinatorial peptide libraries using phage display technology. Various such libraries are commercially available, such as the Ph.D. phage display peptide library kits from New England Biolabs (Beverly, MA; see instruction manual for Catalog #E8100S, available at www.neb.com).

Preferred phage display libraries include stabilized display domains. Such phage display libraries include display domains stabilized by cys-cys disulfide bonds, such as the f88-4/Cys6 library available without restriction from Dr. George Smith (University of Missouri, Columbia, MO, Ref.: RDV50:16 (RB1). See Smith, G.P. & Petrenko, V.A., Phage display, Chem. Rev. 97: 391-410 (1997) and www.biosci.missouri.edu/SmithGP/PhageDisplayWebsite/PhageDisplayWebsiteIndex.html. FIG. 5 is a diagram of the sequence of the display domain of mature pVIII of the f88-4/Cys6 library, showing the amino acid sequence of the display domain of the mature DVIII, SEQ ID NO:1, the nucleotide sequence of the display domain. SEQ ID NO:34, and the nucleotide sequence of the secluencing primer, SEQ ID NO :35.

Phage display denotes a selection technique in which a peptide or protein is recombinantly expressed fused to a coat protein of a bacteriophage, resulting in the display of the fused protein on the surface of the virion, while the DNA encoding the fusion resides within the virion. Phage display thus creates a physical linkage between a vast library of random peptide sequences to the DNA encoding each sequence, allowing rapid identification of peptide ligands for a variety of target molecules (antibodies, enzymes, cell-surface receptors, etc.) by an in vitro selection process called "panning." In its simplest form, panning is carried out by incubating a library of phage-displayed peptides with a plate (or bead) coated with the target, washing away the unbound phage, and eluting the specifically-bound phage. The eluted phage is then amplified and taken through additional binding and amplification cycles to enrich the pool in favor of binding sequences. After 3-4 rounds, individual clones are characterized by DNA sequencing.

Random peptide libraries displayed on phage have been used in a number of applications, including epitope mapping, mapping protein-protein contacts, and identification of peptide mimics of non-peptide ligands. See instruction manual for Catalog #E8100S. Bioactive peptides have been identified either by panning against immobilized purified receptors or against intact cells. Protease substrates have been identified by attaching an affinity tag upstream from the randomized region, and separating cleaved from uncleaved phage with the appropriate affinity matrix. Conversely, larger proteins, such as antibodies, hormones, protease inhibitors, enzymes and DNA binding proteins, have been displayed on phage, and variants with altered affinity or specificity have been isolated from libraries of random mutants. For example, in one embodiment, the Ph.D.-7 Phage Display Peptide Library Kit (New England Biolabs, Beverly, Mass.), which comprises random peptide 7-mers fused to a minor coat protein (pIII) of M13 Phage can be used. Corresponding libraries of 12-mers are also available. The displayed heptapeptides or dodecapeptides, respectively, are expressed at the N-terminus of pIII, i.e., the first residue of the mature protein is the first randomized position. The peptide is followed by a short spacer (Gly-Gly-Gly-Ser) and then by the wild-type pIII sequence. The library consists of $\sim 2.8 \times 10^9$ electroporated sequences (compared to $20^7 = 1.28 \times 10^9$ possible 7-residue sequences), amplified once to yield $\sim 70$ copies of each sequence in 10 µl of the supplied phage. Extensive sequencing of the naive library by the vendor has revealed a wide diversity of sequences with no obvious positional biases.

By comparison, the f88-4/Cys6 library uses the PVIII coat protein of the phage. The f88-4/Cys6 library is stated to have $2.7 \times 10^8$ primary clones, and a DNA size of 9279 bases. FIG. 5 is a diagram of the sequence of the display template of mature pVIII of the f88-4/Cys6 library (SEQ ID NO:1). The concentration of physical particles is $1.87 \times 10^{14}$ virions/ml with an approximate infectivity of 7.7%. In a preferred embodiment, the f88-4/Cys6 library was used as described below in the Examples.

EXAMPLE 1

A study was carried out to identify novel peptides that bind in vitro to a known component of vulnerable plaques, myeloperoxidase. Myeloperoxidase, an abundant leukocyte protein that generates reactive oxidant species, is present and catalytically active within atherosclerotic lesions. A higher concentration of the enzyme myeloperoxidase is a feature that distinguishes vulnerable from stable plaques.

A phage display library of 16 mer cysteine constrained peptides in the display domain of the PVIII coat protein was used to select for peptides with increased affinity for myeloperoxidase and therefore with potential after radiolabeling for diagnostic imaging of unstable plaque. In general, the 16 mer peptides produced have the sequence

SEQ ID NO:2

-Xaa$_1$-Xaa$_2$-Xaa$_3$-Xaa$_4$-Cys$_5$-Xaa$_6$-Xaa$_7$-Xaa$_8$-Xaa$_9$-Xaa$_{10}$-Xaa$_{11}$-Cys$_{12}$-Xaa$_{13}$-Xaa$_{14}$-Xaa$_{15}$-Xaa$_{16}$-

Briefly, the f88-4/cys6 phage library was used for the selection following immobilization of myeloperoxidase on 6-well polystyrene plates. Myeloperoxidase was diluted in 0.1M NaHCO$_2$, pH 8.5 to provide 1-10 µg protein in 400 µl per well. The myeloperoxidase solution was added to the well, swirled to coat the bottom surface, the plate was covered with its lid, secured with parafilm, incubated at room temperature on a rocker for one hour and then stored at 4 degrees Celsius. Each plate included 2 control wells filled with 0.1M NaHCO$_2$ buffer alone and 0.5% HSA in 0.1M NaHCO$_2$ (blocking solution). Prior to panning, the plates were removed from refrigerated storage, the coating solution removed from each well each well filed with blocking solution and incubated at room temperature. Coated wells were then incubated with aliquots of the f88-4/Cys-6 library using a protocol based on that provided by Dr. Smith, with few modifications.

Three rounds of selection were performed. Each round of affinity selection started with a mixture of phage and sought to select from that mixture phase whose displayed peptide binds to the target, in this case, myeloperoxidase. Briefly, after incubation for two hours at room temperature, the blocking solution was removed from the first well (buffer only coating solution), the well was washed five times with Tris-buffered saline (TBS) containing TWEEN® (polvoxvethvlene sorbitan monooleate) and refilled with a solution containing an aliquot of the phage library. The second well (coating solution =blocking solution) was washed five times with Tris-buffered saline (TBS) containing TWEEN® (polyoxvethylene sorbitan monooleate) and after a 30 minute incubation in the first well at room temperature, the phage library solution was transferred to the second well for a 30 minute incubation at room temperature. The third well (myeloperoxidase coated) was washed five times with Tris-buffered saline (TBS) containing TWEEN® (polvoxyethylene sorbitan monooleate) and the phage library solution was transferred from the second well to the third well and incubated for 1 hour at room temperature. After the incubation, the phage solution was removed and saved, and the third well was washed ten times with Tris-buffered saline (TBS) containing TWEEN® (polvoxvethvlene sorbitan monooleate) and bound phage was eluted with 0.1 M glycine buffer pH 2.2 for 15 minutes. The elution buffer was removed and neutralized with Tris HCL buffer pH 9.1. The phage in the glycine eluate were amplified and used for the second round of selection After three rounds of selection, twenty phage clones were sequenced and four peptides occurring in more than one clone were identified. The phage clones representing the four sequences occurring in more than one clone plus a clone having a sequence that occurred in no other selected clone were amplified, titered and conjugated with NHS-MAG$_3$ for radiolabeling with $^{99m}$Tc. See Winnard, P. Jr, et al., Preparation and use of NHS-MAG$_3$ for technetium-99m labeling of DNA, Nucl. Med. Biol. 1997 July; 24(5):425-32. Myeloperoxidase was radiolabeled with $^{125}$I via iodogen and a fixed amount (750 ng) was incubated with a constant number of phage plaque forming units ($10^{10}$) of each of the four consensus clones, plus a non-consensus clone as control, each radiolabeled with $^{99m}$Tc. Myeloperoxidase was added at what was estimated to be a 10-fold molar excess over peptide. After incubating for 15-30 minutes at 4 degrees Celsius, the binding of myeloperoxidase to each phage clone was determined by separating phage from myeloperoxidase using both a MicroSpin S-200 HR spin column and a Sepharose 6B open mini-column. The $^{99m}$Tc counts were used to identify the phage-containing fractions while the 125I counts in those fractions identified the concentration of bound myeloperoxidase. The peptide sequences of the 16 mer cysteine-constrained peptides in the display domain of the PVIII coat protein and the relative binding of four clones (MPO-1, MPO-6, MPO-15 and MPO-17) are listed in Table 2, below.

TABLE 2

SEQUENCES OF THE 16 MER CYSTEINE-CONSTRAINED PEPTIDES IN THE DISPLAY DOMAIN OF THE pVIII COAT PROTEIN

| SEQ ID NO: | Sequence | Phage Clones | Relative Binding |
|---|---|---|---|
| 3 | AMPVCSLDRKACTAYQ | MPO-1 | 3.9% |
| 4 | HVLGCSYATNSCAHNA | MPO-6 | 5.8% |
| 5 | TVMLCNPMEQGCRWMC | MPO-15 | 4.5% |
| 6 | RSGQCHDDTWNCLACV | MPO-17 | 8% |
| 7 | QMKQCWVNTATCWGLS | MPO-4 | |
| 8 | SVEGCTYCDAACEPTL | M3-2 | |
| 9 | ASKYCQMRNYWCGCAG | M3-3 | |
| 10 | LRGQCITRNVSCEPKP | M3-5 | |
| 11 | PSWLCRFEQISCRACH | M3-24 | |
| 12 | QQAVCKQMAYWCGHGN | M3-8 | |
| 13 | PAPRCTVNWDACQMGL | M3-11 | |
| 14 | SKVLCFNYRPTC | M3-16 | |

The peptides expressed by all phage clones having SEQ ID Nos: 3-6 showed some binding to myeloperoxidase; the highest binding was found with phage clone MPO-17. When corrected for the binding associated to the control phage MPO-4, the order of binding was phage MPO-17, MPO-6, MPO-5 and MPO-1 with 8%, 5.8% 4.5% and 3.9% bound, respectively after subtraction of binding by the control phage MPO-4. The peptide expressed by phage MPO-17 was studied further as a potential agent for the scintigraphic detection of myeloperoxidase in vulnerable plaque.

Table 3 shows the structure of the sixteen amino acid residue portions of the display template of mature pVIII of four bacteriophage clones: MPO-1, SEQ ID NO: 3; MPO-6, SEQ ID NO: 4; MPO-15, SEQ ID NO: 5; MPO-17, SEQ ID NO: 6 and a control peptide, MPO-4, SEQ ID NO: 7.

TABLE 3

STRUCTURES OF 16 MER CYSTEINE-CONSTRAINED PEPTIDES

```
MPO- 1 (2 clones)
Ala-Met-Pro-Val-Cys-Ser-Leu-Asp-Arg-Lys-Ala-Cys-Thr-Ala-Tyr-Gln   (SEQ ID NO: 3)

MPO- 6 (3 clones)
His-Val-Leu-Gly-Cys-Ser-Tyr-Ala-Thr-Asn-Ser-Cys-Ala-His-Asn-Ala   (SEQ ID NO: 4)

MPO- 15 (2 clones)
Thr-Val-Met-Leu-Cys-Asn-Pro-Met-Glu-Gln-Gly-Cys-Arg-Trp-Met-Cys   (SEQ ID NO: 5)

MPO- 17 (5 clones)
Arg-Ser-Gly-Gln-Cys-His-Asp-Asp-Thr-Trp-Asn-Cys-Leu-Ala-Cys-Val   (SEQ ID NO: 6)

Control Peptide
Gln-Met-Lys-Gln-Cys-Trp-Val-Asn-Thr-Ala-Thr-Cys-Trp-Gly-Leu-Ser   (SEQ ID NO: 7)
```

Figure 8:
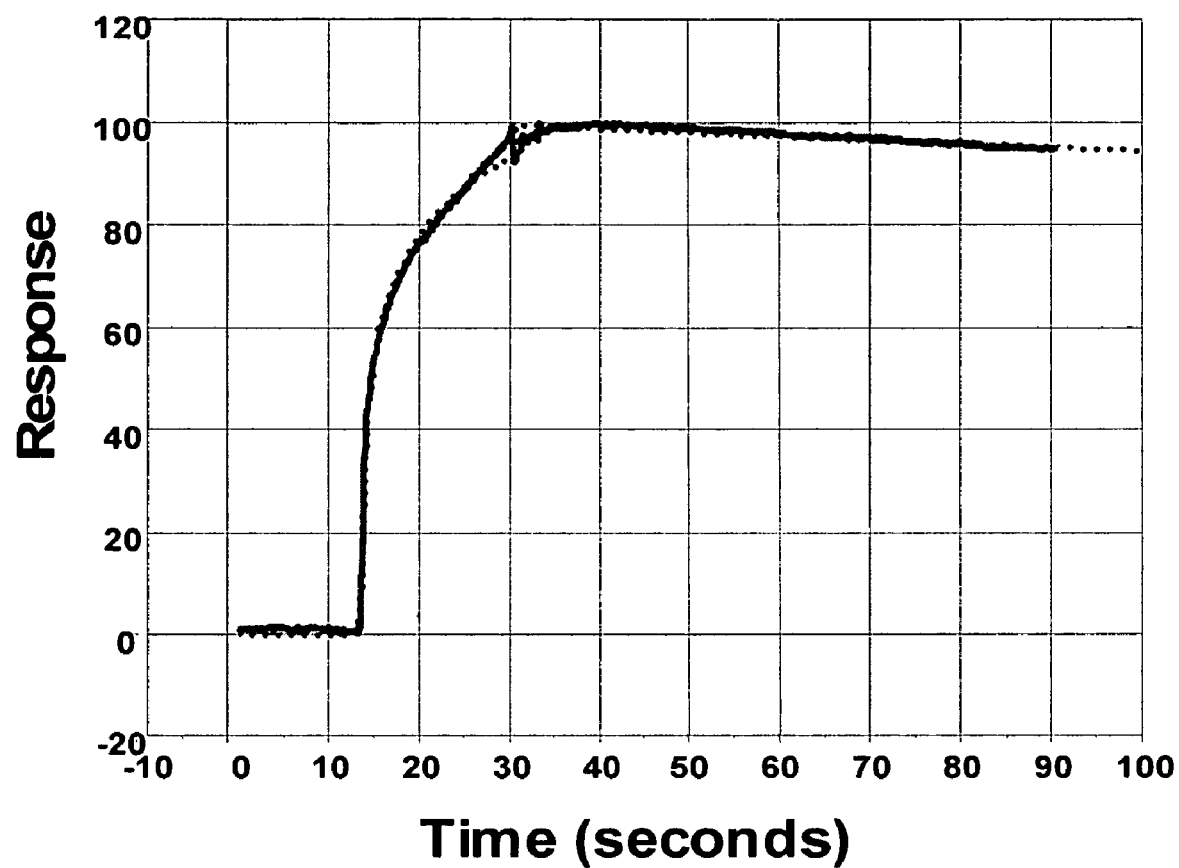
FIG. 8 is a graphical representation of the results of surface plasmon resonance studies. Peptide binding was evaluated by surface plasmon resonance (Biacore 1000) using biotinylated myeloperoxidase immobilized on a streptavidin chip. The MPO-17 twenty-three mer peptide and the twenty-three mer control peptide were applied at a concentration of 1 µM. After subtraction of a sensogram obtained using a control cell, the sensogram shown was obtained (measured, continuous line), from which an affinity constant of about 900 nM was estimated (fitted curve, dotted line).

FIG. 8 is a graphical representation of the results of studies of the binding of several bacteriophage clones to $^{125}$I-myeloperoxidase where the relative magnitude of binding was MPO-17>MPO-6>MPO-15>MPO-1>control (MPO-4). The consensus phage clones were radiolabeled with $^{99m}$Tc, using MAG$_3$ as chelator, and the myeloperoxidase was iodinated using iodogen. The $^{99m}$Tc-phage were incubated with the $^{125}$I-myeloperoxidase for 15-30 minutes, and then separated on a Sepharose 6B column. The shift of $^{125}$I to the higher molecular weight fractions associated with $^{99m}$Tc-phage indicated binding. Phage clones MPO-17, MPO-6, MPO-15, MPO-1 showed binding above the binding of the control clone MPO-4, with the MPO-17 clone showing the highest binding. Based on these data, the MPO-17 peptide was synthesized.

Peptides MPO-17 and the control peptide MPO-4 were synthesized inserting Gly-Gly-Ser as linker and Gly-Gly-Gly-Cys for radiolabeling with $^{99m}$Tc; both were added to the carboxyl end. The peptide was radiolabeled with $^{99m}$Tc, using a tartrate, stannous chloride solution. Labeling efficiency was 50%-60% as determined by Sep Pak using 40% ACN to elute the 99 mTc-peptide. In alternative embodiments, the twenty-three mer peptides were biotinylated; the biotinylated peptides were used in histological studies, described below. Twenty-three mer peptides are synthesized for the other clones using the sequences of the corresponding sixteen amino acid residue display domains and Gly-Gly-Ser-Gly-Gly-Gly-Cys.

Table 4, below, shows the sequences of synthetic twenty-three amino acid residue polypeptides comprising the sequences of SEQ ID NOs 2-12. Table 5, below, provides the structure of four such twenty-three mer synthetic polypeptides

TABLE 4

SEQUENCES OF THE TWENTY-THREE MER CYSTEINE-CONSTRAINED SYNTHETIC POLYPEPTIDES

| SEQ ID NO: | Sequence | Phage Clones |
|---|---|---|
| 15 | RSGQCHDDTWNCLACVGGSGGGC | MPO-17 |
| 16 | QMKQCWVNTATCWGLSGGSGGGC | MPO-4 |
| 17 | AMPVCSLDRKACTAYQGGSGGGC | MPO-1 |
| 18 | HVLGCSYATNSCAHNAGGSGGGC | MPO-6 |
| 19 | TVMLCNPMEQGCRWMCGGSGGGC | MPO-15 |
| 20 | SVEGCTYCDAACEPTLGGSGGGC | M3-2 |
| 21 | ASKYCQMRNYWCGCAGGGSGGGC | M3-3 |
| 22 | LRGQCITRNVSCEPKPGGSGGGC | M3-5 |
| 23 | PSWLCRFEQISCRACHGGSGGGC | M3-24 |
| 24 | QQAVCKQMAYWCGHGNGGSGGGC | M3-8 |
| 25 | PAPRCTVNWDACQMGLGGSGGGC | M3-11 |

Figure 7A:
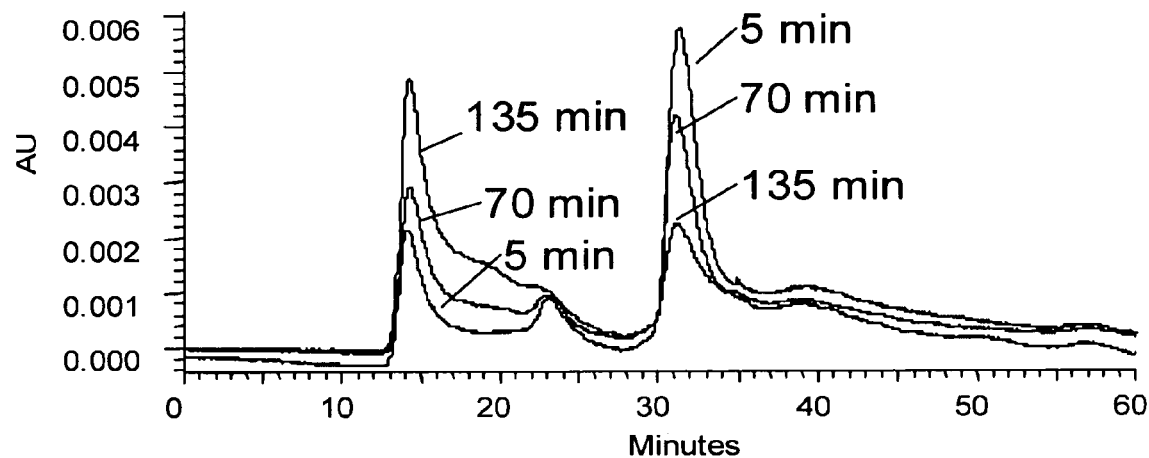
FIGS. 7A and 7B are graphical representations of the results an evaluation of twenty- three mer peptide binding by SE-HPLC using a Superose-12 column.
Figure 7B:
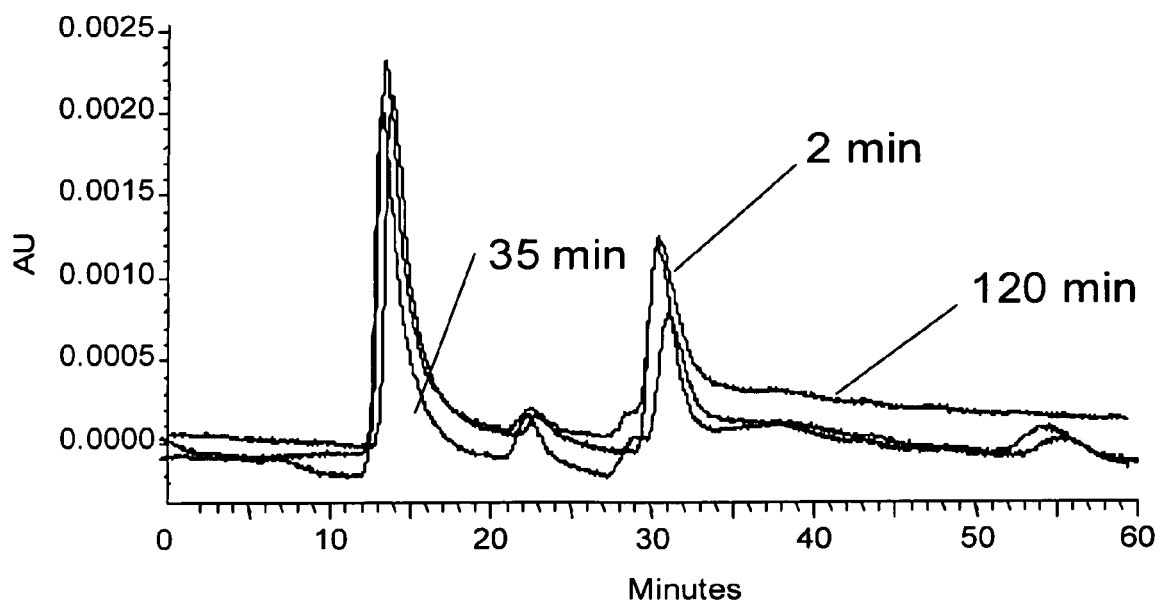

FIGS. 7A and 7B are graphical representations of the results of an evaluation of MPO-17 twenty-three mer polypeptide binding by SE-HPLC using a Superose-12 column. As shown in FIG. 7A, upon incubation of the MPO-17 synthetic polypeptide with the myeloperoxidase, a gradual shift was observed for to a retention time associated with myeloperoxidase. For example, the UV peak for the enzyme increased from 16% of total protein at 5 min of incubation to 46% of total protein after 2 hours incubation. FIG. 7B shows no shift over a comparable time period for incubation of myeloperoxidase with the MPO-4 control twenty-three mer synthetic polypeptide.

TABLE 5

STRUCTURES OF THE MPO TWENTY-THREE MER SYNTHETIC POLYPEPTIDES

MPO-17 (SEQ ID NO:15)
Arg-Ser-Gly-Gln-Cys-His-Asp-Asp-Thr-Trp-Asn-Cys-Leu-Ala-Cys-Val-
Gly-Gly-Ser-Gly-Gly-Gly-Cys

MPO-4 (SEQ ID NO:16)
Gln-Met-Lys-Gln-Cys-Trp-Val-Asn-Thr-Ala-Thr-Cys-Trp-Gly-Leu-Ser-
Gln-Gly-Gly-Ser-Gly-Gly-Gly-Cys

MPO-1 (SEQ ID NO:17)
Ala-Met-Pro-Val-Cys-Ser-Leu-Asp-Arg-Lys-Ala-Cys-Thr-Ala-Tyr-Gln-
Gln-Gly-Ser-Gly-Gly-Gly-Cys

MPO-6 (SEQ ID NO:18)
His-Val-Leu-Gly-Cys-Ser-Tyr-Ala-Thr-Asn-Ser-Cys-Ala-His-Asn-Ala-
Gln-Gly-Ser-Gly-Gly-Gly-Cys

FIG. 8 is a graphical representation of the results of surface plasmon resonance studies. Peptide binding was evaluated by surface plasmon resonance (Biacore 1000) using biotinylated myeloperoxidase immobilized on a streptavidin chip. The MPO-17 twenty-three mer peptide and the twenty-three mer control peptide were applied at a concentration of 1 µM. After inline subtraction using a control cell, the sensogram shown was obtained (measured, continuous line), from which an affinity constant of about 900 nM was estimated (fitted curve, dotted line).

In brief, the myeloperoxidase was bound to a carboxylmethylated (CM) dextran coated surface (or chip) as follows. Using a 1:1 mixture of 1-ethyl-3-(3-diethylaminopropyl) carbodiimide hydrochloride (EDC) and N-hydroxysuccinimide NHS, the myeloperoxidase was applied at pH 4-5.5 and immobilized through the primary amine groups. For measurement of binding constants, the peptide is delivered in 10 mM HEPES, 150 mM NaCl, 3.4 mM sodium EDTA, 0.005% P20, pH 7.4. Each analysis consists of multiple measurements. The association constant ($k_{on}$ or $K_a$) is determined by the rate of binding to the peptide (increase in resonance units (RUs) per unit of time) at different cell concentrations. The dissociation constant ($k_{off}$ or $K_d$) was measured at the end of the association phase with the running buffer at a flow rate of 50 ul/min, to reduce the potential for rebinding during dissociation. The kinetic rate constants are calculated from the sensograms using the instrument software (BIA evaluation 3.0, Biacore) by assuming 1:1 Langmuir interaction in the case of single peptides, and $K_D$ values were calculated from the ratio of dissociation ($k_d$) and association ($k_a$) rate constants. Subtraction of the sensogram obtained with the control chip containing an irrelevant protein from the sensogram obtained with the myeloperoxidase chip at each concentration corrected for bulk refractive index changes.

EXAMPLE 2

Binding partners are selected by differential screening against stable and vulnerable plaques. Screening is performed both for clones identified in in vitro screening against purified plaque components as described in Example 1 as well as screening of the entire library. A phage display library is applied to surgically removed coronary arteries with stable plaques to exclude phage populations which interact with the stable plaques and normal arterial lumen. The remaining unbound phage population is then incubated with the arteries containing vulnerable plaques. The arteries containing vulnerable plaques are washed multiple times under stringent conditions to remove the unbound phage population. The bound phages are collected and propagated by infecting nonpathogenic laboratory bacterial strains. This screening process is repeated a minimum of three times to enrich the interacting phage population. The DNA of the resulting phage populations is individually purified and sequenced to determine the peptide sequences responsible for the interaction with the vulnerable plaque. Peptides corresponding to the sequence of the display region of the phage clones that exhibit specific binding to components of vulnerable are synthesized and labeled as described above in Example 1. The specific interaction of purified phage clones that bind only to vulnerable plaques can be confirmed by immunohistochemical analysis using anti-phage antibodies or by binding of biotinylated synthetic polypeptides as described below.

EXAMPLE 3

The binding of identified peptides to components of plaques was confirmed histologically as follows. Peptide sequences found in multiple selected clones were used to produce peptides using synthetic techniques. Peptides may also be produced using recombinant DNA techniques. The peptides are conjugated with a detectable label, such as biotin using known protocols. The biotin-labeled peptides are used to confirm the binding specificity determined in Example 1 and Example 2 by immunohistochemical analyses of tissue such as vulnerable plaques or tissues rich in components vulnerable plaques that have been exposed to biotin-labeled peptides.

Figure 9A:
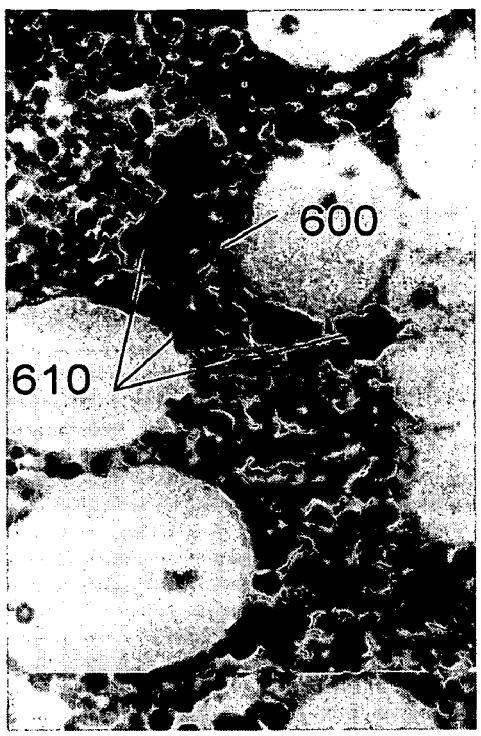
FIGS. 9A-9D show the results of histological studies. Slides of bone marrow tissue were used since they are known to contain myeloperoxidase. Treatments were as follows.
Figure 9B:
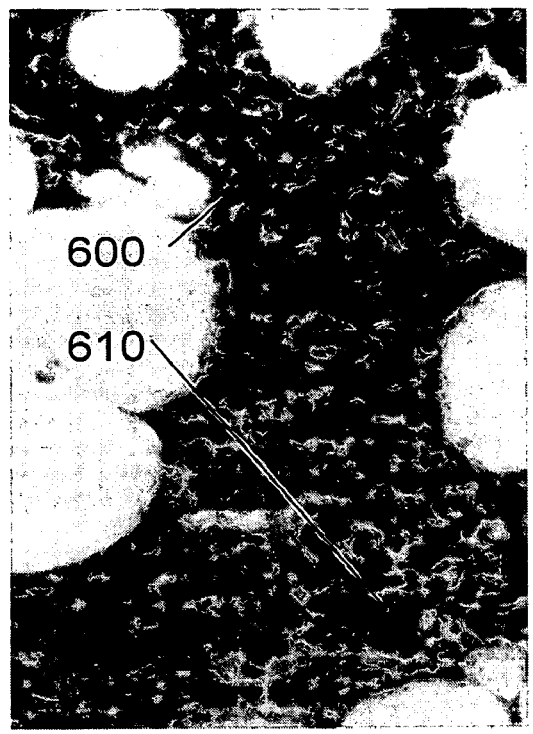
Figure 9C:
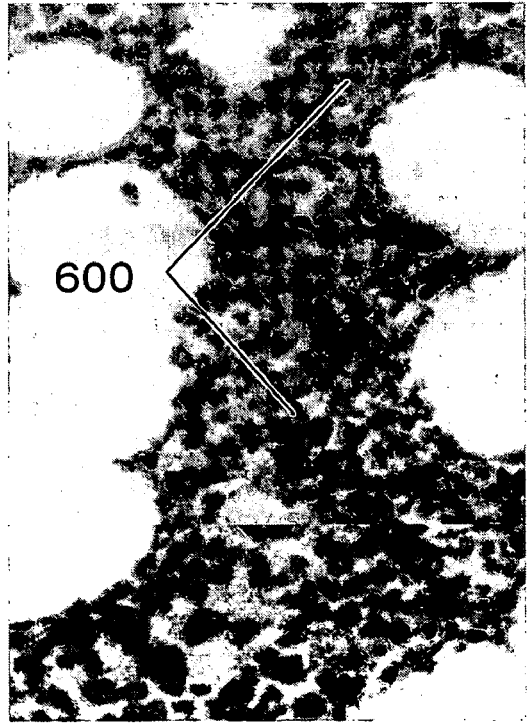
Figure 9D:

FIGS. 9A-9D show the results of such histological studies. Slides of bone marrow tissue were used since they are known to contain myeloperoxidase (above right). Treatments were as follows: FIG. 9A, anti-myeloperoxidase antibody followed with biotinylated secondary antibody; FIG. 9B, biotinylated twenty-three mer MPO-17 peptide; FIG. 9C, biotinylated twenty-three mer control peptide; FIG. 9D, incubated with both the biotinylated twenty-three mer MPO-17 peptide and the biotinylated twenty-three mer control peptide, without primary antibody. Each slide was treated with an anti-biotin antibody and the ABC alkaline phosphatase kit (Vector labs) and counterstained with hematoxylin, which stains nuclei. The anti-myeloperoxidase antibody shows the presence of myeloperoxidase staining (FIG. 9A). Only the hematoxylin stain is observed when the tissue is treated with the control peptide (FIG. 9C) or in the absence of the primary antibody (FIG. 9D). However, treatment with the twenty-three mer MPO-17 peptide produces staining pattern similar to that seen with the anti-myeloperoxidase antibody (FIG. 9B).

EXAMPLE 4

In vivo binding of phage clones and polypeptides identified as described in EXAMPLES 1 and 2 is preformed using a mouse model system. Atherosclerotic plaque formation is induced in apo-E deficient mice by intraperitoneal administration of pro-inflammatory cytokines such as a combination of TNF-alpha, interleukin-1β and interferon-gamma as previously described. See Litovsky, S., et al., Superparamagnetic iron oxide-based method for quantifying recruitment of monocytes to mouse atherosclerotic lesions in vivo: enhancement by tissue necrosis factor-alpha, interleukin-1-beta, and interferon-gamma. Circulation, 2003. 107(11): p. 1545-9, and Naghavi, M., et al., From vulnerable plaque to vulnerable patient: a call for new definitions and risk assessment strategies: Part II. Circulation, 2003.108(15): p. 1772-8. Coronary arteries of cytokine-treated mice are harvested. Immunohistochemistry to show binding of phage clones or polypeptides is performed as described above. In further studies, specific binding is studied in vivo using radiolabeled phage clones or polypeptides and visualization of the interaction with vulnerable and non-vulnerable plaques using combined SPEC/CT or PET/CT.

EXAMPLE 5

Multivalent Peptide Constructs

To increase the peptide's affinity, peptide candidates exhibiting favorable biodistribution (low normal tissue accumulation) and clearance, as well as stability and affinity are each made into multivalent constructs using frameworks such as MAP (multiple antigenic peptides) and polyvalent branched PEG (polyethylene glycol). In addition to increased affinity, these peptide constructs can be an improvement over single peptides by reducing the potential for protease attack and prolonging circulation time, thus increasing the opportunity for binding to the target. As described above in Example 1, the multivalent constructs are evaluated by characterizing and evaluating binding using HPLC and ELISA; measuring the affinity of the multivalent constructs for myeloperoxidase with surface plasmon resonance. The biodistribution and clearance properties are evaluated in normal mice using the techniques of Example 4.

EXAMPLE 6

Studies with TAG-72 Specific Phage

Similar studies have used the f88-4/Cys6 phage display libraries as described above to identify peptides from to the tumor marker TAG-72. In brief, for selection, a solution of the purified TAG-72 was absorbed to wells of a 6-well polystyrene plate (35 mm in diameter, BD Falcon). Additional samples were absorbed to serve for subtraction of non-specific and sticky phage. The eluant from the B72.3 affinity column from the purification of the TAG-72 was free of TAG-72, and 0.5% BSA. Phage were eluted with 0.2 M glycine pH 2.2, and after three rounds of selection isolated phage colonies representing single clones were prepared for DNA sequencing using the in-house nucleic acid core facility. Twenty-three clones from the third round were sequenced using as primer 5'-AGT AGC AGA AGC CTG AAG A-3' (Qiagen, Alameda, Calif.) added at a concentration of 100 pmol/µl. Three consensus peptides were identified from the 23 phage clones.

TABLE 6

SEQUENCES OF THE 16 MER CYSTEINE CONSTRAINED PEPTIDES IN THE DISPLAY DOMAIN OF THE pVIII COAT PROTEIN

| SEQ ID NO: | Sequence | Phage Clones | Relative Binding |
|---|---|---|---|
| 26 | NPGTCKDKWIECLLNG | A3-10 | 4.3 |
| 27 | NLIWCRKEFARCTSDM | A3-19 | 1.5 |
| 28 | LKNYCRKCSNRCTPTG | A3-21 | 1 |
| 29 | MNYYCHQTTKTCRTHS | A3-12 | 1 |

For in vitro studies, LS-174T colon cancer cells, known to express the TAG-72 protein were incubated at a fixed ratio of cells ($6 \times 10^5$ per 50 µl) to $^{99m}$Tc-labeled phage, ~$1.5 \times 10^{11}$ virions. The A3-10 phage clone showed binding that was 4,3-fold higher than the control phage (A3-12). Phage A3-19 also showed elevated binding compared to the control phage (about 1.5-fold). The binding of phage clone A3-21 was similar to that of the control phage clone.

Since TAG-72 expression is known to be higher in solid tumors than cells from culture, LS-174T cells were grown in nude mice, the resulting tumors removed and cut into ~1 mm cubes for an assay using solid tumors. In addition to the labeled phage, the $^{99m}$Tc-labeled antibody was used to evaluate the level of antigen expression in tumor. For assay the tumor cubes were incubated with serial dilutions of $^{99m}$Tc-labeled phage or the $^{99m}$Tc-B72.3 antibody. The A3-10 phage clone showed a linear increase in phage bound with phage added. The control phage, A3-12 showed no change in phage bound except at the highest concentration, indicating specific binding of the A3-10.

To test if phage A3-10 could compete with the B72.3, the LS-174T tumor cubes were incubated with 1 ng of $^{99m}$Tc-labeled B72.3 antibody and serial dilutions of unlabeled A3-10 phage. The activity associated with the binding of antibody decreased with an increase in unlabeled phage added. Thus, the phage is likely blocking the antibody, an indication of binding to the same target.

As described above, twenty-three mer peptides are synthesized inserting Gly-Gly-Ser as linker and Gly-Gly-Gly-Cys for radiolabeling with $^{99m}$Tc; both are added to the carboxyl end. The peptide is radiolabeled with $^{99m}$Tc, using a tartrate, stannous chloride solution. Labeling efficiency is 50%-60% as determined by Sep Pak using 40% ACN to elute the $^{99m}$Tc-peptide. In alternative embodiments, the twenty-three mer peptides are biotinylated; the biotinylated peptides are used in histological studies, described below. The sequences of exemplary twenty-three mer peptides are synthesized for the clones using the sequences of the corresponding sixteen amino acid residue display domains and Gly-Gly-Ser-Gly-Gly-Gly-Cys are provided in Table 7, below.

TABLE 7

SEQUENCES OF TWENTY-THREE MER CYSTEINE CONSTRAINED SYNTHETIC POLYPEPTIDES

| SEQ ID NO: | Sequence | Phage Clones |
|---|---|---|
| 30 | NPGTCKDKWIECLLNGGGSGGGC | A3-10 |
| 31 | NLIWCRKEFARCTSDMGGSGGGC | A3-19 |
| 32 | LKNYCRKCSNRCTPTGGGSGGGC | A3-21 |
| 33 | MNYYCHQTTKTCRTHSGGSGGGC | A3-12 |

The disclosure of every patent, patent application, and publication cited herein is hereby incorporated herein by reference in its entirety.

What is claimed:

1. A method of detecting a vulnerable plaque comprising the steps of:
   providing the isolated polypeptide of SEQ ID NO: 6 or SEQ ID NO: 15 conjugated to a detectable label;
   contacting a vulnerable plaque with the labeled isolated polypeptide; and
   detecting the detectable label thereby detecting the vulnerable plaque.

2. The method of claim 1 further comprising the step of imaging the spatial position of the detected vulnerable plaque.

3. The method of claim 1 wherein a component of the vulnerable plaque is myeloperoxidase.

* * * * *